(12) United States Patent
Killard et al.

(10) Patent No.: US 9,435,788 B2
(45) Date of Patent: Sep. 6, 2016

(54) SYSTEM AND METHOD FOR ANALYSING AND MEASURING AMMONIA LEVELS IN A SAMPLE

(71) Applicant: Dublin City University, Glasnevin (IE)

(72) Inventors: Anthony Killard, Malmesbury (GB); Troy Hibbard, Cincinnati, OH (US); Karl Crowley, Marino (IE)

(73) Assignee: Dublin City University, Glasnevin (IE)

( * ) Notice: Subject to any disclaimer, the term of this patent is extended or adjusted under 35 U.S.C. 154(b) by 0 days.

(21) Appl. No.: 14/434,257

(22) PCT Filed: Oct. 9, 2013

(86) PCT No.: PCT/EP2013/071008
§ 371 (c)(1),
(2) Date: Apr. 8, 2015

(87) PCT Pub. No.: WO2014/056961
PCT Pub. Date: Apr. 17, 2014

(65) Prior Publication Data
US 2015/0260706 A1  Sep. 17, 2015

(30) Foreign Application Priority Data

Oct. 9, 2012 (GB) .................................. 1218082.4

(51) Int. Cl.
*G01N 33/497* (2006.01)
*G01N 27/02* (2006.01)
(Continued)

(52) U.S. Cl.
CPC ............ *G01N 33/497* (2013.01); *A61B 5/082* (2013.01); *A61B 5/097* (2013.01); *G01N 27/021* (2013.01);
(Continued)

(58) Field of Classification Search
CPC .. A61B 5/082; A61B 5/097; G01N 33/0054; G01N 33/497; G01N 27/02; G01N 27/021; G01N 2033/4975; Y10T 436/175383; Y10T 436/25; Y10T 436/25125; Y10T 436/255; Y10T 436/2575; Y10T 436/25875
USPC ....... 436/106, 113, 149, 151, 174, 175, 178, 436/180, 181; 422/82.01, 82.02, 83, 84, 88, 422/90, 98; 600/532, 543; 73/23.3
See application file for complete search history.

(56) References Cited

U.S. PATENT DOCUMENTS 3,622,278 A * 11/1971 Elzinga ............. G01N 33/4972
422/84
4,947,861 A   8/1990 Hamilton
(Continued)

FOREIGN PATENT DOCUMENTS

WO   2004/028366 A1   4/2004
WO   2012/045560 A2   4/2012
WO   2012/125745 A2   9/2012

OTHER PUBLICATIONS

Crowley et al. Talanta, vol. 77, Jul. 23, 2008, pp. 710-717.*
(Continued)

*Primary Examiner* — Maureen Wallenhorst

(57) ABSTRACT

A system for sensing and measuring ammonia in a breath sample is described. The system includes a sampling means for capturing and directing a breath sample from a subject to an ammonia sensor, the ammonia sensor including a conducting polymer polyaniline sensor. The sampling means includes a breath sample capture chamber, the chamber having an inlet and outlet, the inlet having a first valve through which a breath is exhaled into the sample capture chamber, the outlet having a second valve through which breath surplus to the volume of the chamber is expelled, to provide capture of a breath sample of predefined volume.

25 Claims, 26 Drawing Sheets

(51) Int. Cl.
 *A61B 5/08* (2006.01)
 *A61B 5/097* (2006.01)
(52) U.S. Cl.
 CPC .......... *G01N 2033/4975* (2013.01); *Y10T 436/175383* (2015.01); *Y10T 436/255* (2015.01); *Y10T 436/25875* (2015.01)

(56) References Cited

U.S. PATENT DOCUMENTS 7,101,340 B1 9/2006 Braun
2010/0000883 A1* 1/2010 Morrin .................. C12Q 1/001
 205/786
2010/0089772 A1* 4/2010 Deshusses ........... G01N 27/127
 205/781

OTHER PUBLICATIONS

M M L Steeghs et al.; "An off-line breath sampling and analysis method suitable for large screening studies"; Physiological Measurement, Institute of Physics Publishing, Bristol, GB; vol. 28, No. 5, May 1, 2007; pp. 503-514.

Alvaro Diaz Aguilar et al.; "A Breath Ammonia Sensor Based on Conducting Polymer Nanojunctions"; IEEE Sensors Journal, IEEE Service Center, New York, NY; vol. 8, No. 3, Mar. 1, 2008; pp. 269-273.

International Preliminary Report and Written Opinion in PCT/EP2013/071008 dated Apr. 14, 2015.

* cited by examiner

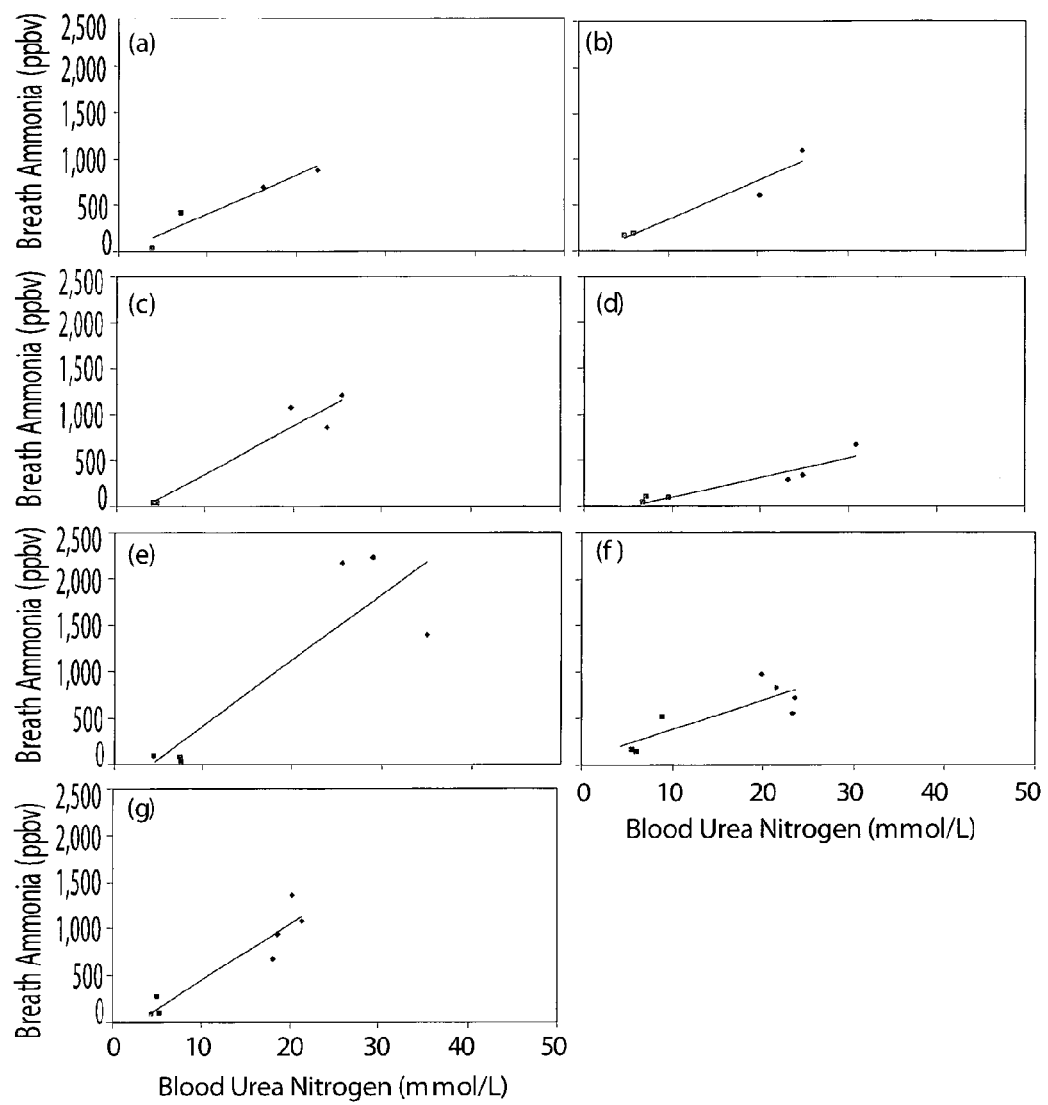
Figure 23 (a-g) Pre-dialysis (blue diamond) and post-dialysis (red square) of intra-individual absolute breath ammonia and blood urea nitrogen concentrations.

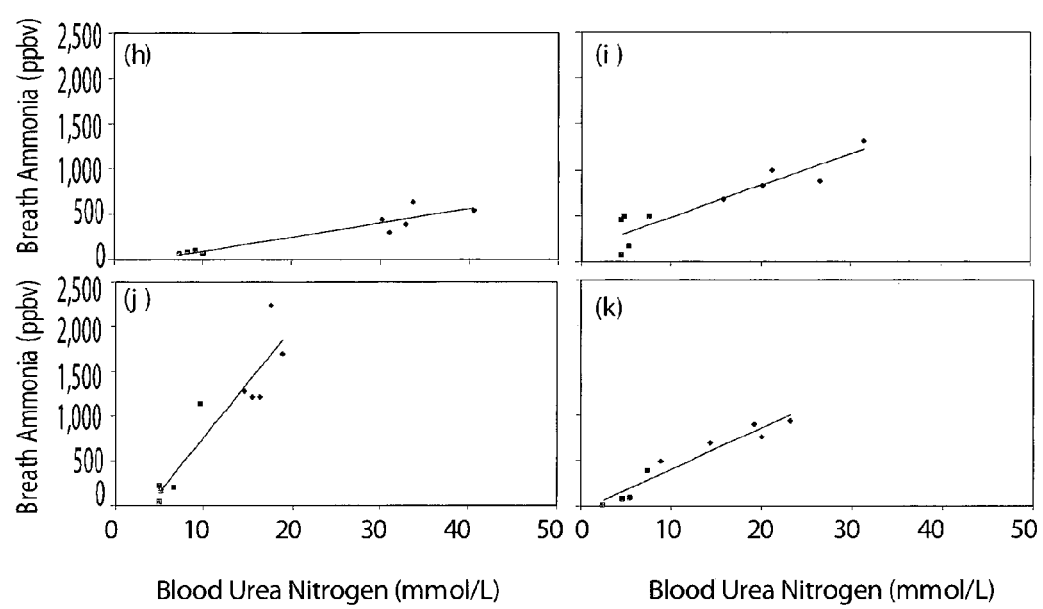
Figure 23 (h - k) Pre - dialysis (blue diamond) and post - dialysis (red square) of intra- individual absolute breath ammonia and blood urea nitrogen concentrations:

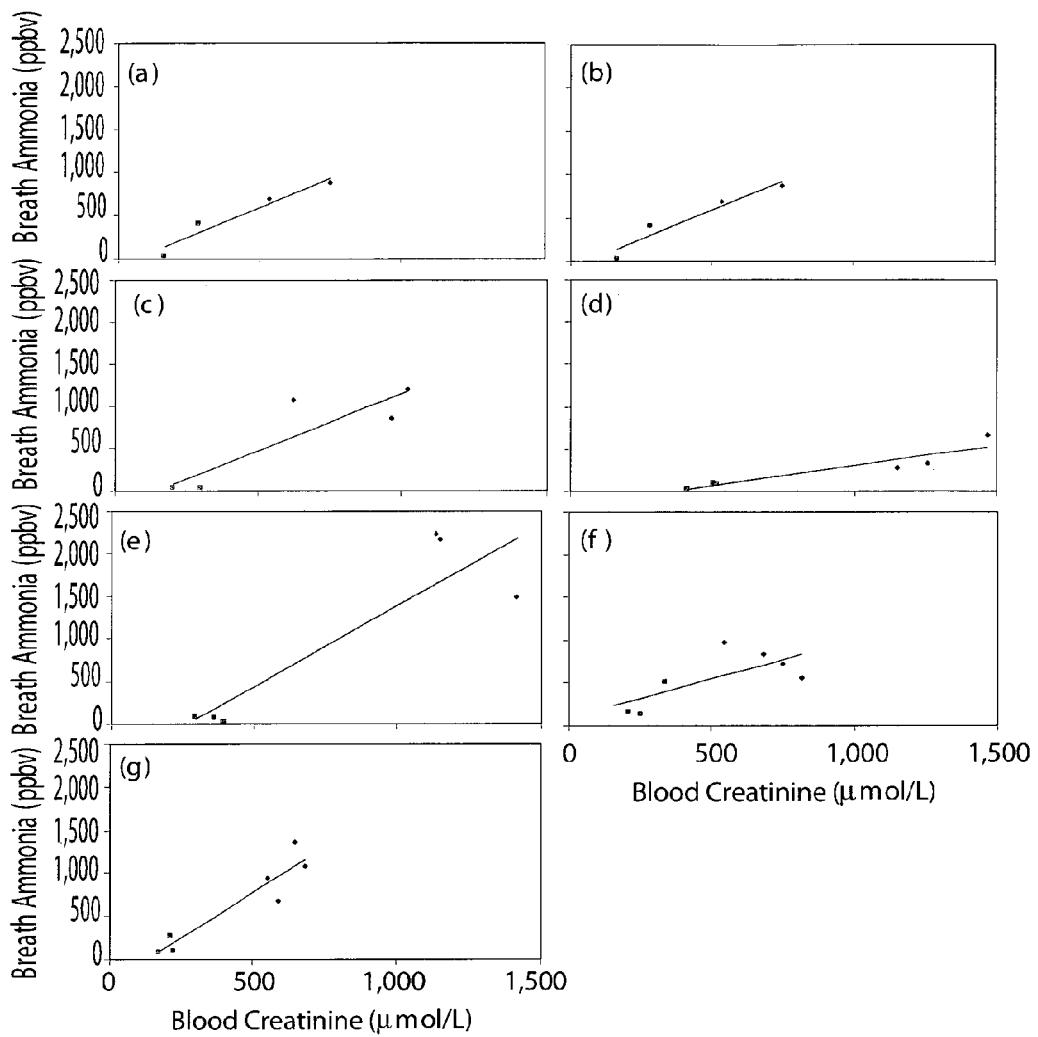
Figure 24 (a - g) Pre - dialysis (blue diamond) and post - dialysis (red square) of intra-individual absolute breath ammonia and blood creatinine concentrations:

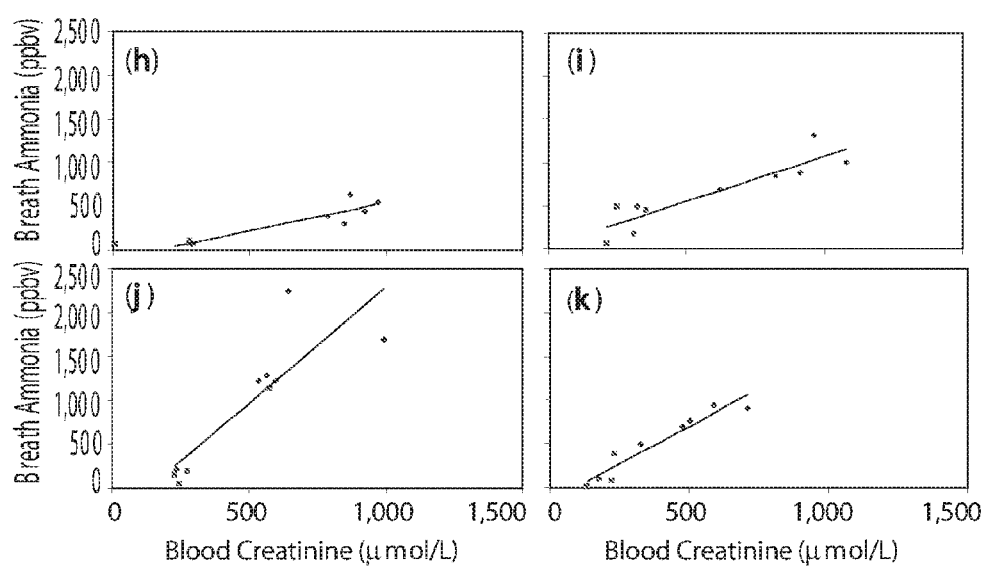
Figure 24 (h-k) Pre - dialysis (blue diamond) and post - dialysis (red square) of intra- individual absolute breath ammonia and blood creatinine concentrations:

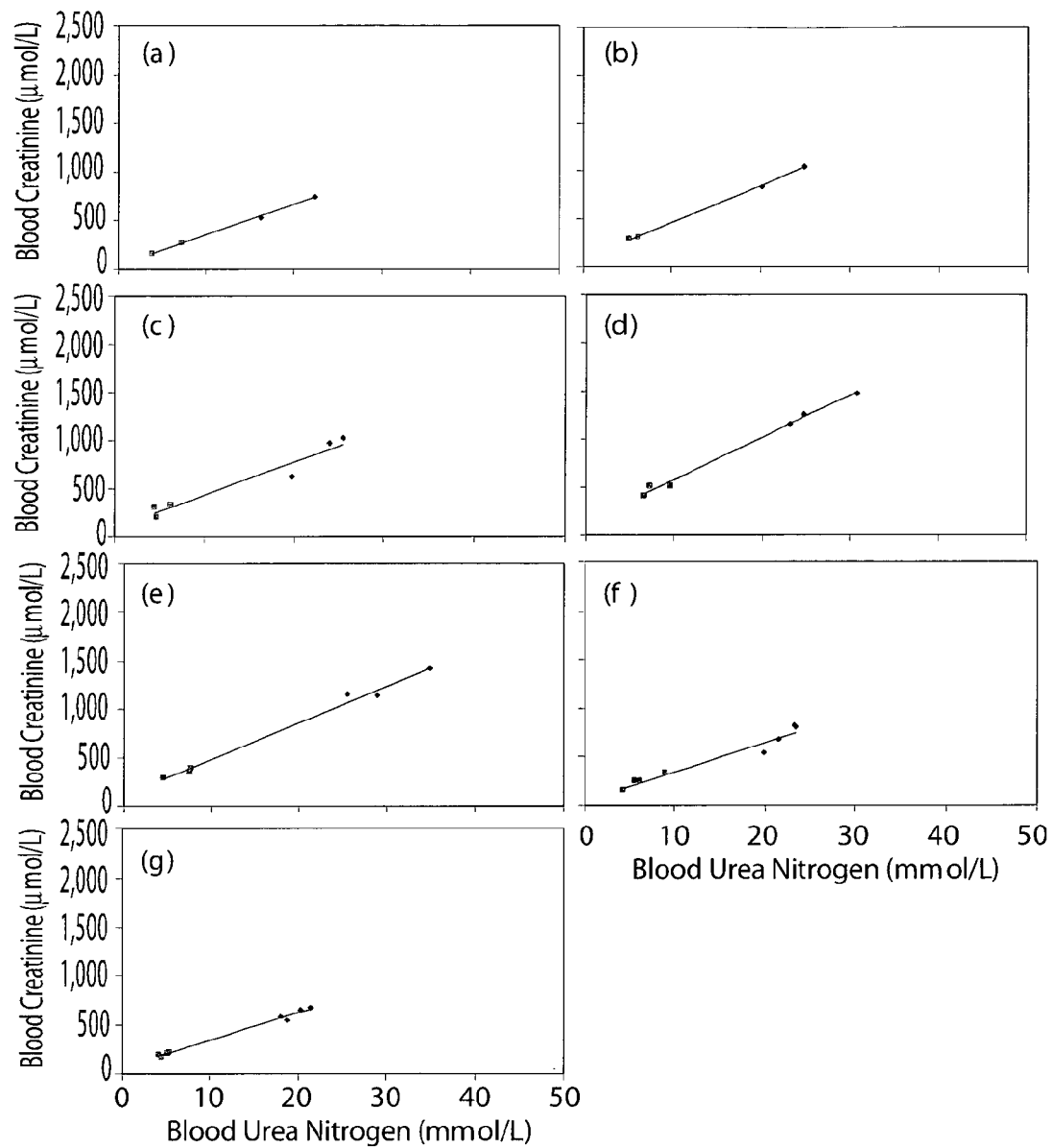
Figure 25 (a - g) Pre - dialysis (blue diamond) and post - dialysis (red square) of intra- individual blood creatinine and blood urea concentrations:

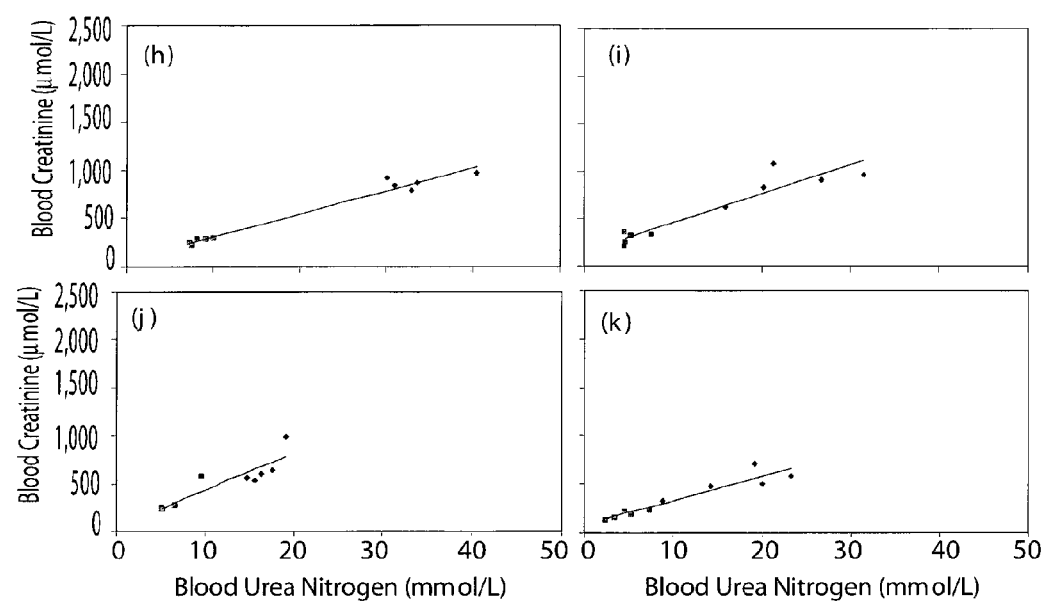
Figure 25 (h-k) Pre-dialysis (blue diamond) and post-dialysis (red square) of intra-individual blood creatinine and blood urea concentrations:

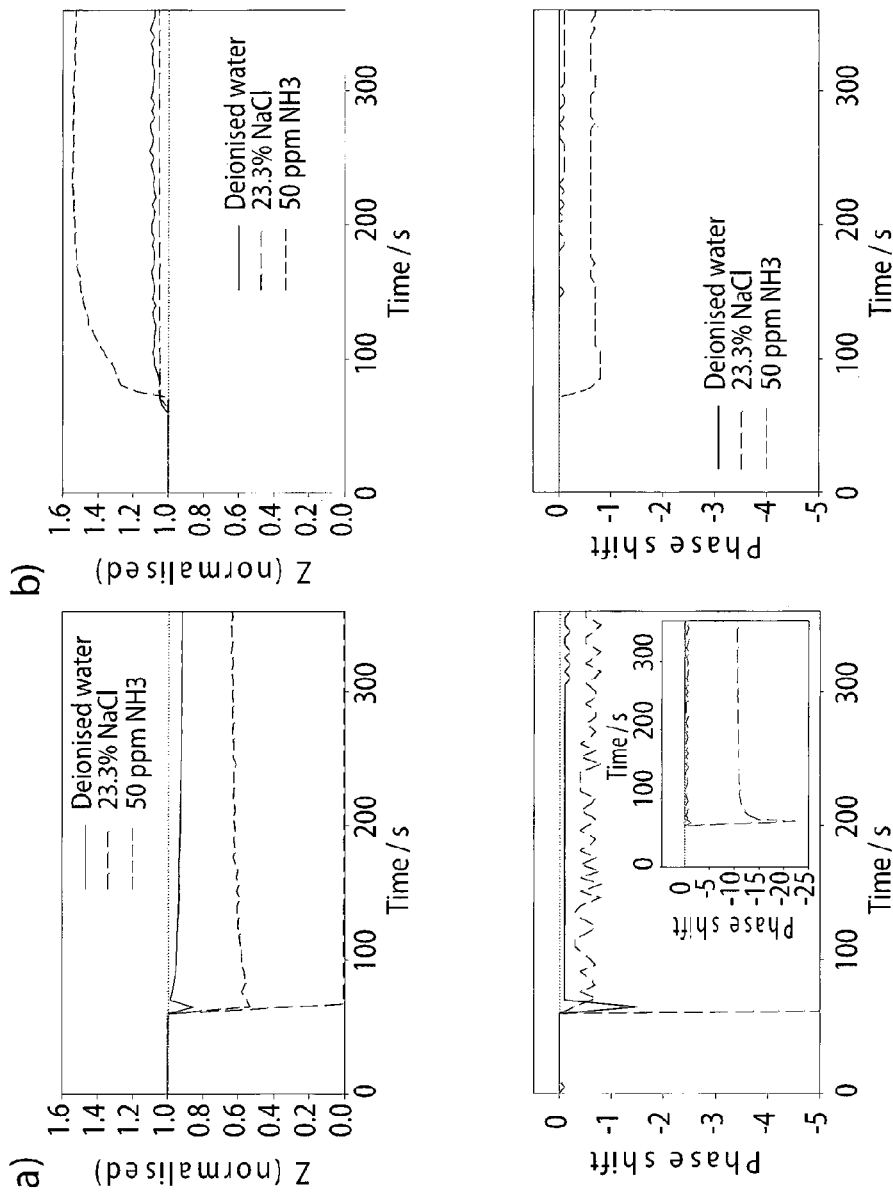
Figure 27. Impedance/time plots observed for (a) an unmodified PANI sensor and (b) a PANI-PTFE sensor to deionised water, 23.3% w/v NaCl in water and 50ppm ammonia in water (100μL droplets on sensor). Impedance parameters: Einit: 0V, Eamp: 5mV, f = 962 Hz, tsample = 5s.

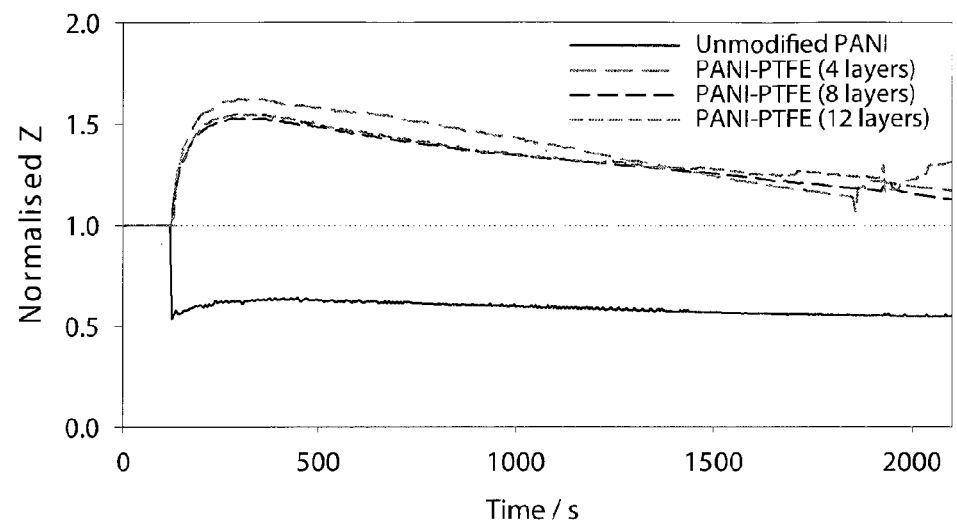
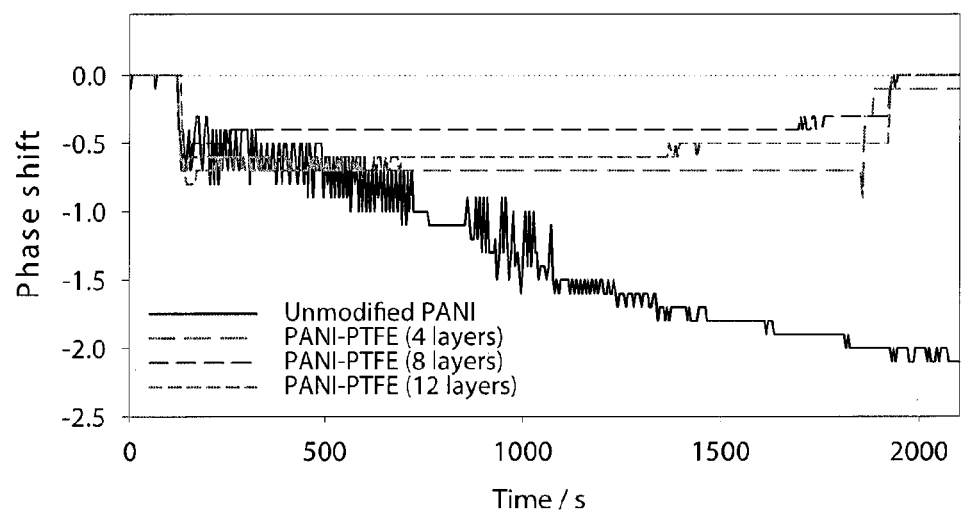
Figure 28. Impedance time plots displaying the effect of 50 ppm ammonia on PANI films modified with different print thicknesses of PTFE particles.

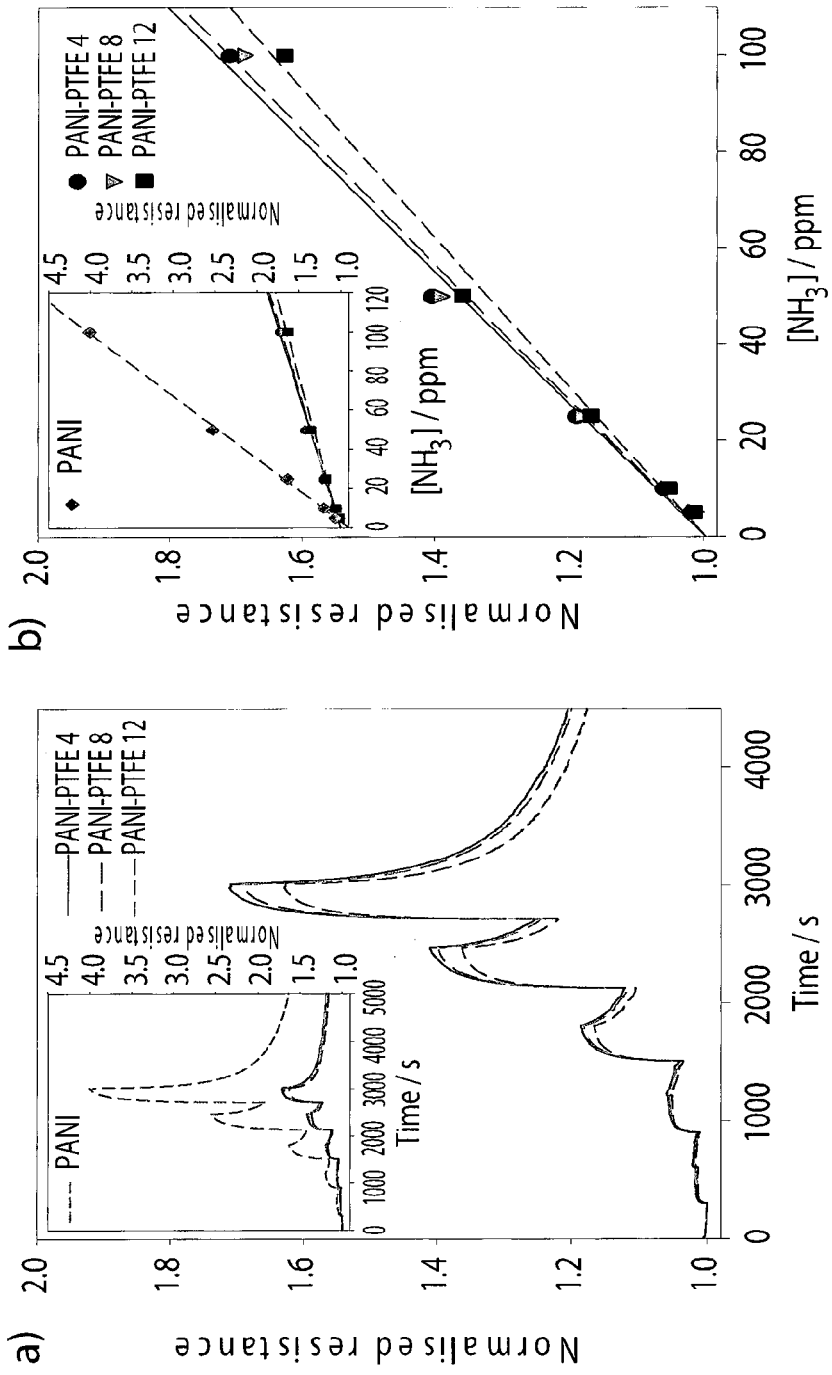
Figure 29. Resistance/time (a) and calibration graphs (b) obtained for PANI modified with different print thicknesses of PTFE. The insets compare the response of the modified and unmodified PANI sensors.

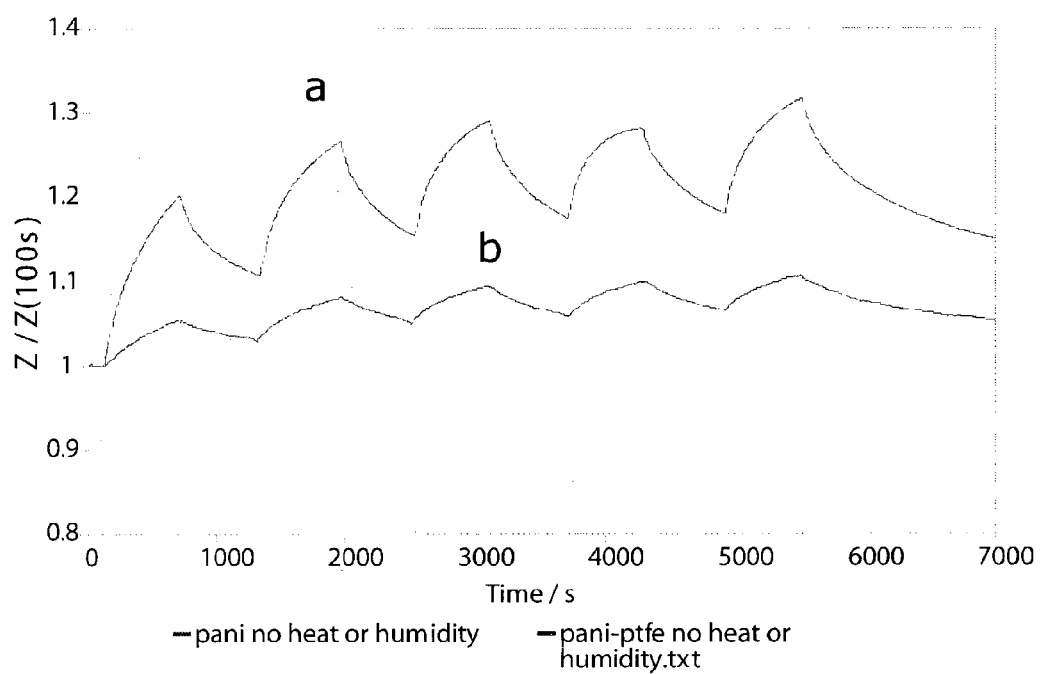
Figure 30. Impedance time plots for sensors in the flow system. Ambient conditions with a mean flow rate of 53.4 l min$^{-1}$. Five sequential exposures to 280 ppb ammonia (10 minutes on,10 minutes off) were performed.  a. PANI no heat or humidity b. pani -ptfe -no heat or humidity Figure 31a. Response of PTFE-modified (10 μm resolution of 4 and 8 layers) and Figure 31b Response of an unmodified PANI sensor to. Ten exhales performed starting at 300s and at 30s intervals thereafter. a) Impedance-time and b) phase angle-time.

SYSTEM AND METHOD FOR ANALYSING AND MEASURING AMMONIA LEVELS IN A SAMPLE

FIELD

The present invention relates to a system and method for analysis and measurement of ammonia levels in a sample and in particular, a system and method for the measurement of ammonia in exhaled breath.

BACKGROUND

Current techniques for measurement of ammonia levels in a patient rely on invasive tests for example, blood tests. Elevated ammonia levels in blood samples are often indicators of issues with the renal system (liver and kidneys). In addition to being invasive, blood testing is also a relatively slow testing method. Typically a sample must be sent to a laboratory for analysis. It may take hours or days for results to be provided to a patient. Further it is normally necessary that testing be performed by a skilled medical practitioner and that access is available to a laboratory.

There is therefore a need to address these and other problems and limitations relating to testing and sampling of ammonia levels in a patient. There is a need to for a more efficient and reliable and sensitive testing method and approach that addresses the above noted problems. Further, there is a need for improved testing system that operates with short analysis time and provides improved accuracy of measurement of analytes in a sample. There is further a need for improved point of care testing systems that are robust and easy to operate.

The present specification aims to address these problems and to provide a non-invasive method and device for monitoring of ammonia levels in breath which has been shown to correlate with blood levels and is a simple and non-invasive means of testing.

SUMMARY

According to the present specification there is provided a system for sensing and measuring ammonia in a breath sample, comprising a sampling means for capturing and directing a breath sample from a subject to an ammonia sensor, the ammonia sensor comprising a conducting polymer polyaniline sensor.

In particular, there is provided a system according to claim 1. The system comprises further optional features according to claims 2 to 23. There is further provided a point of care testing device according to claim 24 or 25.

The sampling means may comprise a breath sample capture chamber, the chamber having an inlet and outlet, the inlet having a first valve through which a breath is exhaled into the sample capture chamber, the outlet having a second valve through which breath surplus to the volume of the chamber is expelled, to provide capture of a breath sample of predefined volume.

The sampling means may comprise directing means for directing the breath sample of predefined volume from the capture chamber across the ammonia sensor. The directing means may be operable to direct the breath sample of predefined volume across the sensor at a predefined volume flow rate.

The response from the sensor is preferably proportional to the ammonia concentration in the breath sample.

The system may comprise measuring means for measuring change in conductivity or impedance of the sensor on exposure to ammonia in the breath sample, the change in conductivity or impedance being indicative of ammonia concentration in the breath sample.

The sensor may comprise a polyaniline nanoparticle based material. The sensor may comprise a polyaniline composite. The sensor may comprise a PANI-silver composite. The sensor may comprise a PANI-carbon nanotube composite.

The sensor may be integrated with a heater configured in operation to control the response characteristics of the sensor to ammonia. The sensor may comprise a membrane layer for protecting the sensor from the interferent of humidity in the breath sample while allowing detection of ammonia. The sensor may comprise a membrane layer for controlling the humidity response of the sensor. The membrane layer may be in the form of a pre-fabricated membrane. The membrane layer may be a printable membrane layer. The membrane layer may be of a membrane material impermeable to water molecules. The membrane layer may be of polytetrafluoroethene, or other polymer material permeable to ammonia gas and having water repellent properties. The membrane layer may comprise a solubilised polymer or of a suspension of micro- or nanoparticles. The particles may dispersible in aqueous solvents and annealeable to form a continuous film application of heat, and/or light energy and/or chemical treatment.

The volume of the capture chamber system may be of the order 0.25 to 0.5 of the average human non-forced exhalation of breath.

The sampling means may comprise displacement means configured to provide displacement of any air or other sample present in the sample capture chamber prior to capture of a breath sample. The sampling means may further include a sampling interface for interfacing with the subject whose breath is to be sampled, the sampling interface comprising a mask or spirette. A bacterial or viral filter may be provided located between the interface and sample capture chamber.

According to a further aspect, a point of care testing device according to the present specification is provided. The point of care testing device comprises a system for sensing and measuring ammonia in a breath sample, wherein the device is configured to provide a real time measurement of the concentration of ammonia in a breath sample.

According to a further aspect, a point of care testing device comprising a system for sensing and measuring ammonia in a breath sample of the present specification is provided, wherein the device is configured to provide a continuous monitoring of ammonia in a breath sample over a period of time.

The present specification also provides a method of sensing ammonia in a breath sample comprising, providing an ammonia sensor comprising a polymer polyaniline sensor capturing a breath sample of predefined volume directing the breath sample of predefined volume across the sensor, measuring the response of the sensor to ammonia in the breath sample.

Measuring response of the sensor further comprises measuring change in conductivity or impedance of the sensor on exposure to ammonia in the breath sample, the change in conductivity or impedance being proportional to the ammonia concentration in the breath sample. Directing the breath sample across the sensor comprises directing the breath sample across the sensor at a defined volume flow rate. The directing the breath sample across the sensor comprises alternatively comprises directing the breath sample at a measurable volume flow rate.

The method may further include measuring the flow rate using sensor means. The method may further include calculating instantaneous flow rate and further using processing algorithms to relate instantaneous flow rate to response of the sensor. Further, the directing the breath sample across the sensor at the pre-defined volume flow rate provides a defined rate of ammonia interaction with the sensor. Further the directing the breath sample a predefined volume flow rate prevents humidity condensing onto the sensor. Preferably, the directing of the breath sample at a predefined and continuous flow rate provides a defined response from breath humidity that can be differentiated from the response to ammonia. The method may comprise removing interferences from oral breath delivered to the sampling chamber. The method may comprise capturing and measuring a greater fraction of alveolar air. Further the method may provide that the resulting sensor response results in a response signature particular to responses to heat, humidity and ammonia. Further the method may provide that the response to ammonia can be determined in the presence of thermal and humidity effects.

The sensor may be operated in amperometric (dc) mode. The sensor may be operated in impedimetric mode. Preferably, operation in impedimetric mode allows differentiation of response from interferents such as humidity by employing the different responses of ammonia and humidity to changes in electrode resistance and capacitance.

According to a further aspect, the specification provides a sensor comprising a membrane layer for controlling the humidity response of the sensor. The membrane layer may be in the form of a pre-fabricated membrane. The membrane layer may be a printable membrane layer. The membrane layer may be of a membrane material impermeable to water molecules. The membrane layer may be of polytetrafluoroethene, or other polymer material permeable to ammonia gas and having water repellent properties. The membrane layer may comprise a solubilised polymer or of a suspension of micro- or nanoparticles.

BRIEF DESCRIPTION OF THE DRAWINGS

The present invention will now be described with reference to the accompanying drawings in which:

FIG. 23 (a-g) Pre-dialysis (blue diamond) and post-dialysis (red square) of intra-individual absolute breath ammonia and blood urea nitrogen concentrations: (a) Volunteer 1: r=0.96, p<0.05, n=4 (b) Volunteer 2: r=0.96, p<0.05, n=4 (c) Volunteer 3: r=0.96, p<0.01, n=5 (d) Volunteer 4: r=0.94, p<0.01, n=6 (e) Volunteer 5: r=0.88, p<0.05, n=6 (f) Volunteer 6: r=0.82, p<0.05, n=7 and (g) Volunteer 7: r=0.94, p<0.01, n=7.

FIG. 23 (h-k) Pre-dialysis (blue diamond) and post-dialysis (red square) of intra-individual absolute breath ammonia and blood urea nitrogen concentrations: (h) Volunteer 8: r=0.93, p<0.01, n=9 (i) Volunteer 9: r=0.86, p<0.01, n=10 (j) Volunteer 10: r=0.93, p<0.01, n=10 and (k) Volunteer 11: r=0.96, p<0.01, n=9.

FIG. 24 (a-g) Pre-dialysis (blue diamond) and post-dialysis (red square) of intra-individual absolute breath ammonia and blood creatinine concentrations: (a) Volunteer 1: r=0.96, p<0.05, n=4 (b) Volunteer 2: r=0.97, p<0.05, n=4 (c) Volunteer 3: r=0.89, p<0.05, n=5 (d) Volunteer 4: r=0.93, p<0.01, n=6 (e) Volunteer 5: r=0.88, p<0.05, n=6 (f) Volunteer 6: r=0.71, p=0.074, n=7 and (g) Volunteer 7: r=0.94, p<0.01, n=7.

FIG. 24 (h-k) Pre-dialysis (blue diamond) and post-dialysis (red square) of intra-individual absolute breath ammonia and blood creatinine concentrations: (h) Volunteer 8: r=0.92, p<0.01, n=9 (i) Volunteer 9: r=0.85, p<0.01, n=10 (j) Volunteer 10: r=0.86, p<0.01, n=10 and (k) Volunteer 11: r=0.95, p<0.01, n=9.

FIG. 25 (a-g) Pre-dialysis (blue diamond) and post-dialysis (red square) of intra-individual blood creatinine and blood urea concentrations: (a) Volunteer 1: 1.00, p<0.01, n=4 (b) Volunteer 2: 1.00, p<0.01, n=4 (c) Volunteer 3: 0.97, p<0.01, n=6 (d) Volunteer 4: 1.00, p<0.01, n=6 (e) Volunteer 5: 1.00, p<0.01, n=6 (f) Volunteer 6: 0.98, p<0.01, n=8 and (g) Volunteer 7: 1.00, p<0.01, n=8.

FIG. 25 (h-k) Pre-dialysis (blue diamond) and post-dialysis (red square) of intra-individual blood creatinine and blood urea concentrations: (h) Volunteer 8: 0.99, p<0.01, n=10 (i) Volunteer 9: 0.94, p<0.01, n=10 (j) Volunteer 10: 0.90, p<0.01, n=10 and (k) Volunteer 11: 0.95, p<0.01, n=10.

FIG. 28. Impedance time plots displaying the effect of 50 ppm ammonia on PANI films modified with different print thicknesses of PTFE particles.

FIG. 29. Resistance/time (a) and calibration graphs (b) obtained for PANI modified with different print thicknesses of PTFE. The insets compare the response of the modified and unmodified PANI sensors. Each inject and vent performed at 300 s intervals and sequential inject/vent cycles performed for 5, 10, 25, 50 and 100 ppm. Experimental parameters: Fixed potential; +0.1V applied, data normalised with respect to baseline value at 270 s.

FIG. 30. Impedance time plots for sensors in the flow system. Ambient conditions with a mean flow rate of 53.4 l $min^{-1}$. Five sequential exposures to 280 ppb ammonia (10 minutes on, 10 minutes off) were performed. a. PANI no heat or humidity b. pani-ptfe-no heat or humidity FIG. 31a. Response of PTFE-modified (10 µm resolution of 4 and 8 layers) and FIG. 31b Response of an unmodified PANI sensor to. Ten exhales performed starting at 300 s and at 30 s intervals thereafter. a) Impedance-time and b) phase angle-time.

DETAILED DESCRIPTION OF THE DRAWINGS

Figure 1:
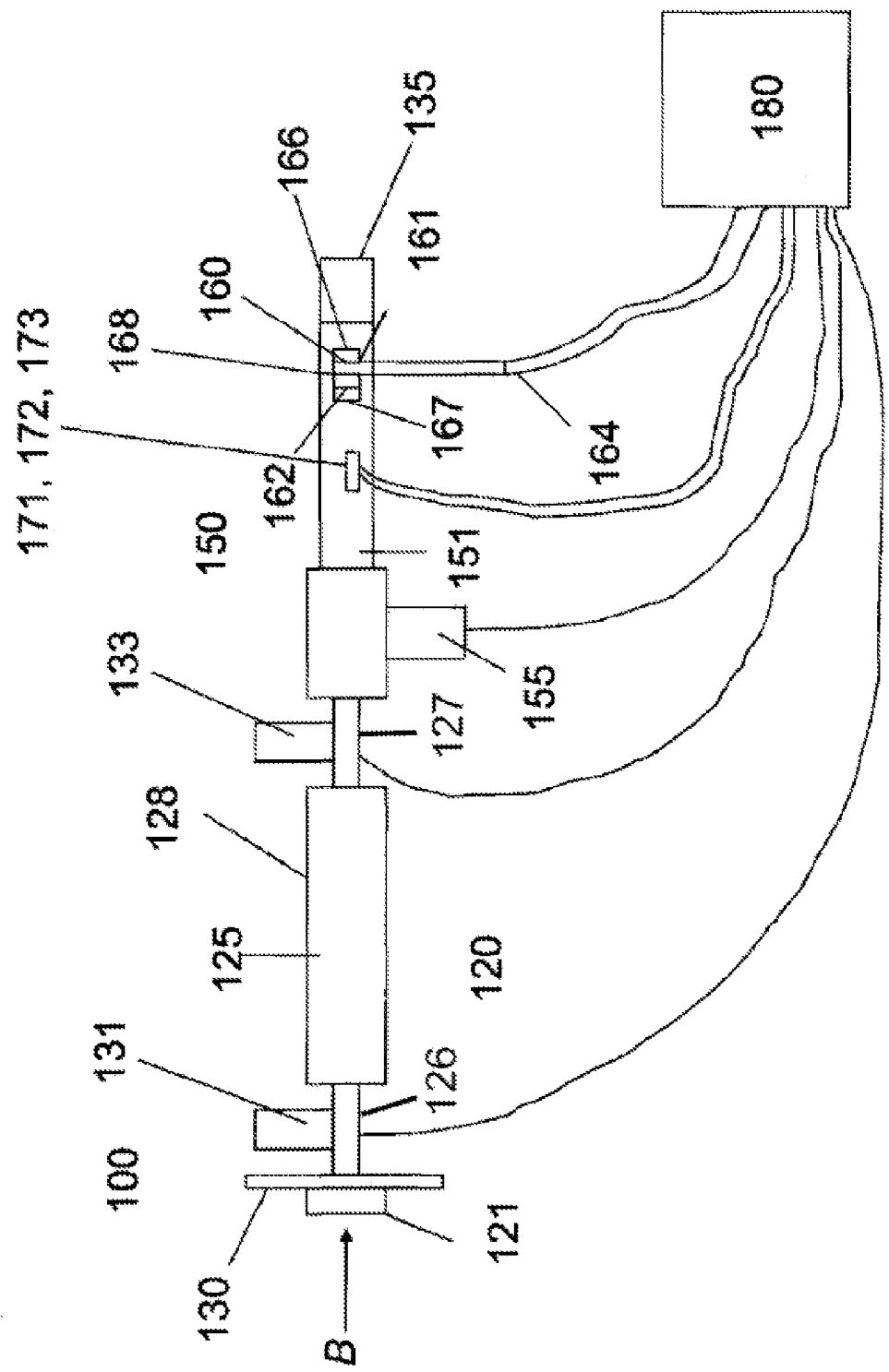
FIG. 1 is a schematic diagram of an exemplary breath sensing system according to the present specification.

Referring to the drawings and initially in particular FIG. 1 a breath analysis system 100 is described. It will be appreciated that the specifics of this breath analysis system 100 are provided to assist in an understanding of the present teaching and in no way should be construed as limiting the teaching to this example.

The breath analysis system 100 comprises a sampling means 120 and a sensing and measuring means 150. The breath analysis system 100 further comprises an instrumentation/control/data processing means 180. The present specification further provides a method for sampling and analysing ammonia in a breath sample. The system 100 and method also provide sampling and data processing methodologies which allow for accurate and reliable breath ammonia measurements to be performed while discriminating against interferences from other species within the breath matrix.

The sampling means 120 comprises an interface 121 and a sample collection chamber 125. The sampling means 120 is configured to collect a sample of breath for analysis.

The sensing and measuring means 150 comprises a sensing chamber 151 housing a sensor 160. The sensor is an ammonia sensor. The sensor 160 is a conducting polymer sensor. The sensing and measuring means 150 is configured to measure change in conductivity or impedance of the conducting polymer sensor 160 on exposure to ammonia in a breath sample.

In more detail, the sensor 160 is a conducting polymer polyaniline sensor which includes a substrate 161 and a sensing film 162. The sensing film 162 comprises a polyaniline nanoparticle film. The sensor 160 further includes an electrical connector 164. The sensor 160 of the exemplary arrangement is based on the inkjet printed deposition of polyaniline nanoparticles as described in patent applications including EP 2004840 and US 20100008831.

Figure 2:
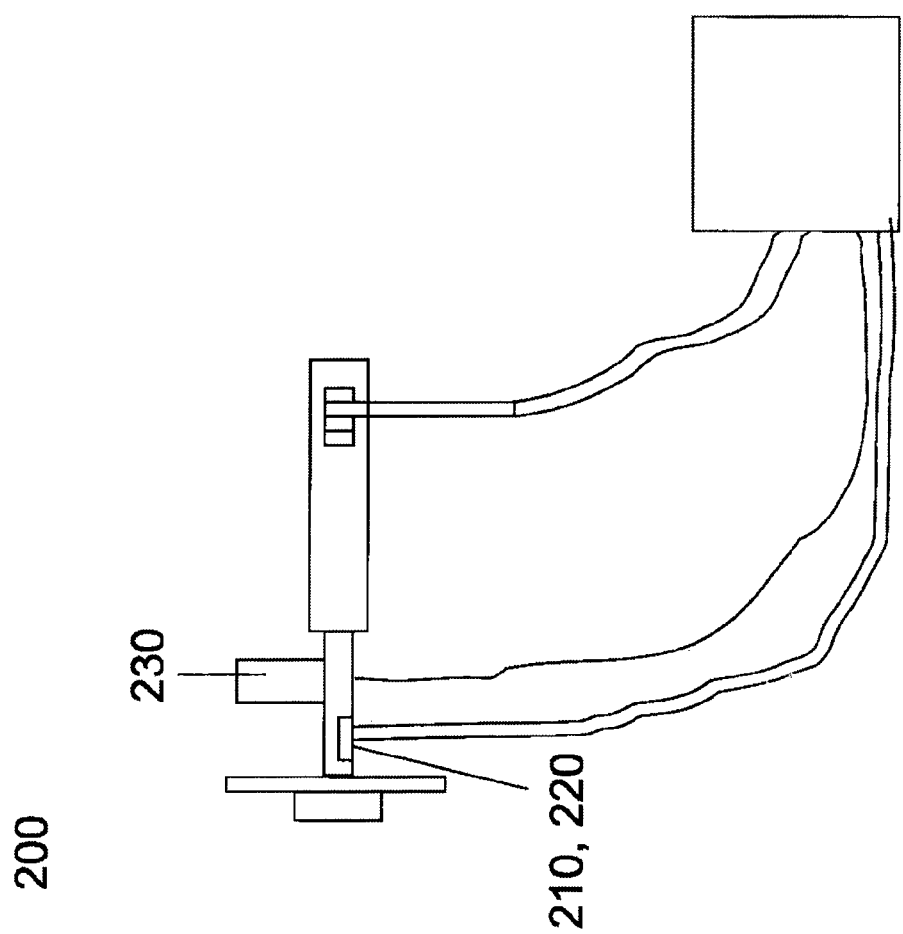
FIG. 2 is a schematic diagram of an exemplary breath sensing system according to the present specification.

In a preferred arrangement according to the specification, the performance and manufacturability of the conducting polymer sensor 160 is advantageously based on use of nanoparticles and their application to inkjet printed deposition. In a preferred exemplary approach according to the present specification electrodes 165 comprising interdigitated electrodes are fabricated by printing silver ink onto a 175 μm thick polyethylene terephthalate (PET) plastic substrate 122. A DEK-248 screen printer utilised a screen with a 45° printing angle with respect to the squeegee at 28 μm porosity to generate the pattern. Once the electrode 165 is prepared, polyaniline (PANI) is ink-jet printed onto the interdigitated portion (FIG. 2). Polyaniline nanoparticles are synthesised by initially adding 3.4 g of 0.25 M dodecylbenzene sulfonic acid (DBSA) to 40 mL of deionised water. DBSA is a dopant which helps with development of the spherical conformation of the polyaniline particles. This may be stirred at room temperature (20° C.) until the DBSA fully dissolved. The solution was divided into two 20 mL solutions. Into the first DBSA solution, 0.36 g of ammonium persulfate (APS) was added and stirred until fully dissolved. APS is an oxidant that polymerises the aniline monomers. Secondary formation resulting in particles too large to be printed from the cartridge is prevented by using the correct ratio of DBSA and APS to aniline. Into the second DBSA solution, 0.6 mL of distilled aniline was added. Quickly, the DBSA-APS solution was added to the DBSA-aniline solution. Using a stir plate and stir bars, the final mixture was allowed to mix rapidly for 2.5 hours. A solution of 0.05 M sodium dodecyl sulphate (SDS) was prepared during the 2.5 hours by dissolving 14.4 g SDS in 1 L of deionised water. SDS quenches and separates particles in order to prevent aggregation. After 2.5 hours, 20 mL of the SDS was added to the PANI/DBSA solution which appeared thick and dark green in colour. The PANI/DBSA/SDS solution was then centrifuged at 5,000 rpm for 30 minutes. During centrifugation, multiple dialysis tubes of 30 cm in length were placed into heated deionised water to soften them. The supernatant from the centrifuged PANI/DBSA/SDS was then poured into 20 cm of each dialysis tubing and sealed off leaving a 2 cm gap. The polyaniline filled tubing was then placed into 500 mL of 0.05 M SDS for 48 hours using the porosity of the tubing to remove excess materials such as unreacted aniline. The final product consisting of nanoparticles of approximately 150 nm in size could then be ink-jet printed onto the electrode by using the Dimatix Drop Manager Ink-jet printer (FUJIFILM Dimatix Inc., Santa Clara, Calif.). Preparation of the printer involved using a Norm-Jet Syringe combined with an Acrodisc polyvinylidene fluoride (PVDF) Syringe Filter (0.45 μm) and needle to inject 1.5 mL of polyaniline into a Fuji Dimatix ink cartridge. The cartridge was placed into the Dimatix ink-jet printer at a head angle of 9.1° and a stage height of 1.2 mm. Fuji Dimatix ink cartridges contained 16 nozzles that ejected 10 L of ink each via a piezoelectric voltage of 22 V. After printing 10 polyaniline layers, the sheets of dry sensors were lightly rinsed with deionised water to remove any excess SDS that may reside since too much SDS surfactant can interfere with conductivity and analytical performance. To ensure that the deionised water was fully removed afterwards, and the sensors were acclimated to higher temperatures, they were placed in a dry-heat oven at 70° C. for 30 minutes. Afterwards, the electrodes 165 were cut from the excess PET, and ready to use for electrochemical analysis.

In the sensing and measuring means 150, the sensor 160 may be integrated with a heater 166. Heater 166 is configured to actively control the response characteristics of the sensor 160 to ammonia. The response to ammonia from the sensor is temperature dependent, which affects the kinetics of the association and dissociation of the ammonia with the film. Increasing the temperature significantly increases the rate of dissociation time of the ammonia from the sensor and so shortening recovery time. Temperature control can also be used to compensate for changes in ambient temperature, as well as reducing interferences such as condensation of water vapour onto the electrode. A number alternative of heating arrangements 166 may be envisaged for interfacing with the sensor, for example, solid state heater devices may be employed, as might be heaters fabricated using printed heater inks to complement the fabrication methods used for electrode production.

A membrane layer 167 may be applied to the sensor electrode 165. The membrane layer 167 is configured to exclude the interferent of humidity present in breath, while still allowing detection of ammonia. Various alternative forms of the membrane layer 167 are provided. The membrane layer 167 may be in the form of a pre-fabricated membrane. The membrane layer 167 may be based on a printed membrane layer. This membrane layer 167 may be of a membrane material that is impermeable to water molecules. The membrane layer 167 may comprise polytetrafluoroethene, also known as PTFE (Teflon™). The membrane layer 167 may comprise other similarly water repellent polymers which remain permeable to ammonia gas. The membrane layer 167 may be a printable membrane layer. The membrane layer may be composed of solubilised polymer or of a suspension of micro- or nanoparticles, each of which are amenable to deposition and film formation using a range of deposition methods including printing, and spin coating. The particles may additionally be dispersible in aqueous solvents and can be annealed to a continuous film by techniques such as the application of heat, light energy or chemical treatment.

The ammonia sensing film 162 in the exemplary arrangement of the present specification is composed of polyaniline nanoparticles as described previously for example in EP 2004840, US 20100008831. The polyaniline nanoparticle ink composition may be composed of additional materials to form composites 168. Composites 168 are engineered to provide good analytical response characteristics, while also remaining amenable to the original process methodologies, such as ink jet printing and other deposition methodologies.

Composites 168 including a PANI-silver composite or PANI-carbon nanotube composite, are provided. These composites 168 provide improved analytical response characteristics including improved sensitivity and improved response and recovery times.

The sensor 160 may be disposable. For example, sensor 160 may be configured for use for a single measurement or defined sequence or period of measurements.

The sampling means 120 is configured for collecting and transferring a breath sample B from a patient to sensor 160.

The sampling means 120 includes a sampling interface 121 for interfacing with the subject whose breath is to be sampled. The sampling interface 121 may be a mask 122 or spirette 123 to interface with a patient or subject to collect oral and/or nasal breath samples.

The sampling means 120 includes a sample capture chamber 125 for collecting a sample of predefined volume V. The sample capture chamber 125 includes an inlet 126 which is connected to the sampling interface 121 and an outlet 127 to allow the escape of the collected breath sample B. The sample capture chamber 125 includes walls 128 to contain the breath sample B.

The breath analysis system 100 further includes directing means 135 operative to direct or transfer the captured breath sample B from the sample capture chamber 125 across the sensor 160. The directing means may comprise a fan.

The sampling means 120 may include 'T' valves 131 and 133 to allow inhalation and exhalation while connected to the sampling interface 121 and an additional membrane or filter 130 to prevent bacterial contamination into and back from the sampling system.

The system 100 may further include heater 166 and/or temperature probe 171 and/or humidity probe 172 and/or flow probes 173, as required. The heater 166, and probe/s as required, may be provided in the sensing chamber 151. The sensing chamber 151 may optionally include other components such as air valves 155 (active or passive) and/or fan 135 to control the movement of the breath sample across the surface of sensor 160. The location and orientation of the sensor 160 in sensing chamber 151 and the form of the chamber 151 are engineered to optimise characteristics of the sensing chamber 151 to provide a strong interaction between the sensor 160 and the flow of breath sample B relative to the sensor 160 (FIG. 3).

The configuration of the breath analysis system 100 takes account of the sensor type, the complexity of the breathing protocol, the complexity of the valving, flow control and sensing chamber 151 arrangement and the signal processing methodology.

The breath analysis system 100 of the present specification advantageously provides means to measure a known volume V of a breath sample B over a known time period T, and thus, known volume flow rate. Further, the system 100 provides reduction or exclusion of interferences to measurements and to the analysis from the effects of temperature, humidity and other volatile gasses. Further advantageously, the system 100 provides means for the measurement of breath ammonia in a breath sample in 'real time'.

The breath analysis system 100 may further be configured to be disposable/semi-disposable following an appropriate period of use or number of uses.

Breath analysis system 100 further comprises instrumentation and control means 180 for controlling operation of the breath analysis system 100 and sensor 160. Control means 180 provides electrical control of the active components of the system and the sensor 160. System 100 further comprises data processing and measuring means 190 for providing processing and/or measurement of responses from the sensor 160.

Operation of the sensor 160 requires application of a controlled potential of either a dc (amperometric) or ac (impedimetric) form. Measurement of ammonia in a breath sample is performed by either operating the system in amperometric (dc) mode 200 or impedimetric mode 210. In amperometric (dc) mode 200, the response of the sensor 160 to ammonia is essentially ohmic (resistive) in nature. It is noted that in this mode of measurement chemical changes to the film 164 may result. Further in a two electrode configuration, the real potential can deviate from the applied potential.

In impedimetric mode 210, a small potential perturbation is applied to the sensor 160. In addition, the mean potential is zero, which does not lead to polarisation of the film or subsequent chemical changes. Impedimetric mode 210 is further suitable for operation in two electrode mode for measurement of gaseous samples. Further, impedimetric measurement allows improved differentiation of response from interferents such as humidity by employing the different responses of ammonia and humidity to changes in electrode resistance and capacitance, as it has been shown that the sensor responses to ammonia are purely resistive in nature below approximately 1000 Hz, whereas responses to humidity also show capacitive characteristics which can be seen by analysing changes in phase angle. Impedimetric mode can be selectively employed depending on the sampling method and sensor surface modification method employed.

The instrumentation and control means 180 includes a potentiostat 181 configured to apply an ac or dc potential or appropriate magnitude and waveform. For dc, a magnitude from 0 to up to 1 V has been employed. For dc, a small ac signal of some millivolts is typically applied (5 to 100 mV) with a waveform of either a sinusoidal or square wave form. However, square waveforms may be used as well as sinusoidal waveforms and are easier to create in low cost electronic instrumentation than sinusoidal. A range of ac frequencies are also suitable. Operation at a frequency of the order of 1 kHz has been found advantageous. As stated earlier, it has been shown that at or below approximately 1 kHz, the changes in response to ammonia are purely resistive in nature, which can be readily measured using absolute impedance ($|Z|$).

The instrumentation and control means 180 may further include timers 182 and/or actuators 183 to switch on and off valves as appropriate. The instrumentation and control means 180 further comprises drive means 184 for driving fan 156 as required, most preferably at a fixed potential. This is to ensure constant and reproducible fan speed and so constant and reproducible flow rate of sample through the fan and across the sensor.

The instrumentation and control means 180 includes an electronic logic system to allow the programming of electronic functions. It also requires the monitoring of the applied signal and response from the electrode, whether ohmic or impedimetric. In the latter case, the ability to monitor the phase and amplitudes of the applied voltage and the resulting current is required to determine the real and imaginary impedances at any time. This approach assists in elimination of sensor response due to humidity. As changes in phase angle only occur for humidity at certain frequencies, this can be used to differentiate between the changes in signal due to ammonia and humidity in the sample.

The instrumentation and control means 180 includes memory and data processing means 190 to provide conversion of the electrical signals from the sensor 160 into data and/or values of ammonia concentration. Ammonia concentration is provided for display to a user in an appropriate way. Further, storage means 195 is provided for storing data, as required.

The instrumentation and control means 180 and data processing means 190 are re-usable with sampling means 120 and sensor 160, and sensing means 150, which as noted above may be disposable or semi-disposable, for example, after a predefined number of uses.

Analytical measurement as provided using breath analysis system 100 is based on the principle that there is a defined concentration of analyte within a given volume or mass of matrix in which the sample is present. This is also the case of ammonia in exhaled breath. Sampling means 120 is configured to capture and transfer a breath sample obtained from the subject being sampled to the sensor 160 in a controlled and defined manner. Variables considered include sample volume and/or the flow rate and/or number of breaths and/or breath temperature and/or humidity and/or the presence of interferent gasses/species.

A breath is not a defined sample in terms of volume, flow rate, or flow profile, neither is it consistent from breath to breath or person to person. System 100 is configured to take account of, and exclude such variability. Breath analysis system 100 of the present specification is configured to control and define the volume of a breath sample by providing for capture of a volume of breath sample in the sample capture chamber 125 at atmospheric pressure. The sampling means 120 is configured to capture a breath sample S of volume V corresponding to the volume of the sampling capture chamber 125 without altering its content. The sampling means 120 includes displacement means 135 configured to fully displace any previous air or sample present in the sample capture chamber 125. The displacement means is configured in use to simplify the analytical measurement process as each breath sample B has a defined and reproducible volume.

The sampling system 100 further mechanical means 135 for example a fan configured in operation to define the sample flow rate across the sensor 160.

Referring to FIG. 1 an exemplary breath analysis system 100 and method of operation of the device is described. System 100 comprises sampling means 120 and sampling interface 121 including spirette mouth piece 122. Attached to the spirette mouth piece is a bacterial or viral filter 130. Filter 130 does not impede sample flow or modify sample composition, but prevents transfer of bacteria to or from the sampling means 120.

The sampling means 120 includes a first 'T' valve 131 which is configured to allow exhaled breath to transfer to the sampling capture chamber 121 and to allow air to be inhaled without release of the spirette 122 from the mouth, or to allow fresh air to transfer to the sampling means.

The breath sample is transferred to sample capture chamber 121 via 'T' valve 132. Sample capture chamber 121 has a volume of 170 ml in the exemplary arrangement of FIG. 1a. The sample capture chamber 121 defines the sample volume of the breath sample B before application of the breath sample to sensor 160. The sample capture chamber 121 volume is of the order of a factor of four smaller than the average human non-forced exhalation of some 500 ml. While in the above the volume of the capture chamber is 170 ml, of the order or quarter the volume of the average human non-forced exhalation, it will be appreciated that suitable alternative capture volumes of the order of between 0.25 and 0.5 of the average human non-forced exhalation may also be provided. The volume of the sample capture chamber 121 is so provided to account for inconsistencies among human exhalations. Further, the arrangement provides a capture of a sample of predefined volume. As the user exhales, surplus breath and the previous contents of the chamber are expelled through 'T' valve 133.

This valve 133 can be either active or passive depending on design requirements. The exhalation of surplus breath taken at the beginning of the exhalation reduces the contamination of the breath sample from orally produced gases such as those generated by oral bacteria. In addition, the capture of the end of the exhalation contains more of the alveolar air sample, which contains higher concentrations of the released gases following gaseous exchange.

This sampling capture chamber 125 is connected to a sensing and measuring chamber 151 via valve 1552. Valve 155 may be an active or passive valve as required. In the sensing chamber 151 ambient air is drawn across the sensor 160 via fan 135 without altering its content. This allows a sensor 'baseline' to be determined which is based on the content and constituents of the ambient air, in terms of its background ammonia content, its humidity and its temperature. Thus, the response of the sensor has been defined relative to the ambient conditions of operation prior to sampling. Further details of the performance and behaviour of the fan are given below under Example 1 below (where result data from operation of an exemplary system 100 according to the present specification are discussed). The arrangement of the system 100 and the method of capturing and transferring a breath sample B across the sensor with a defined and constant flow rate as provided by the fan 135 and between breaths, ensure a defined rate of ammonia dissociation from the sensor 160.

When the valve 152 is actuated, air stops flowing in from outside and the 170 ml sample of breath is drawn across the sensor 160 and electrode 165 at the pre-defined volume flow rate. This results in a response from the sensor 160 proportional to the ammonia concentration in the breath sample. Control of flow of the sample across the sensor 160 as provided by system 100 and the method of the present specification importantly prevents humidity condensing onto the sensor 160. Humidity would interfere with sensor performance. This prevention of condensation is distinct from the response of the sensor to humidity in the breath sample. However, membrane layer 167 as described may also be provided to address humidity, as would measurement of phase angle in combination with magnitude in impedimetric operational mode. Condensation is prevented by maintaining a constant flow velocity of the sample across the electrode, followed by the flow of ambient (normal humidity) air, as well as having the sensor in a configuration perpendicular to the flow vector. As well as preventing permanent condensation of water vapour, this configuration also leads to a defined response characteristic of the humidity influence on the sensor which can be differentiated from the effect of ammonia.

Referring to FIG. 2, in another example arrangement according to the present specification, the breath analysis system 200 is provided, the system 200 may be operated as follows. Pressure 210 and/or air flow 220 sensors in the measurement chamber can monitor instantaneous air flow rates. Detection of an exhalation by the patient could lead automatically to the switching of actuated valves 230 to allow sample collection. During exhalation and following an appropriate period to allow oral air to be vented to the atmosphere by 230, the breath sample could be directed across the sensor without the aid of a directing means such as a fan. During this, the breath flow rate and volume would be measured by the sensors 210 and 220 to allow the measured signal due to ammonia to be quantified. As the air flow is no longer continuous, alternative means of preventing condensation such as a membrane layer would prove more beneficial in this scenario. In addition, additional measurement using phase angle could be employed to differentiate between humidity and ammonia as a defined time-based response signature such as that generated using constant flow rate may not be achievable. Following the exhalation, the air flow sensors would detect the cessation of breath sample and redirect the air flow as necessary.

The specification provides a system for isolating and detecting the concentration of gaseous ammonia from breath, using the conducting polymer polyaniline. An ink-jet printable aqueous dispersion of polyaniline nanoparticles has been developed which can be dispersed across a flexible electrode substrate for the purpose of analyte detection Examples and Experimental Result Data Exemplary arrangements of breath analysis system 100 and method according to the present specification are described as follows:

An exemplary system for sensing and measuring ammonia in a breath sample according to the specification was provided. Referring to the drawings and in particular initially FIGS. 3 and 4 results based on operation of the device were noted. In Figures showing comparative results, the results for the breath analysis system 100 according to the specification are referenced as Amber (A device for measuring ammonia in breath).

Figure 3A:
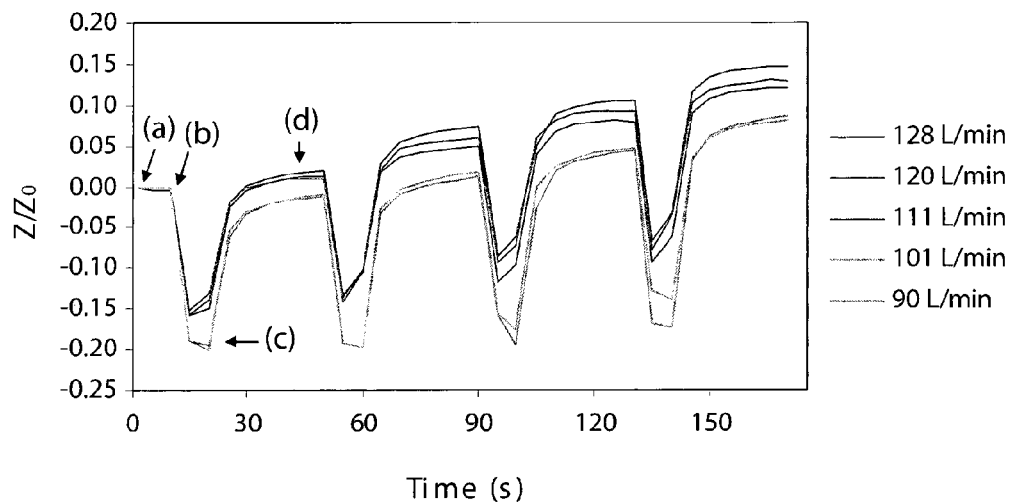
FIG. 3A. A simulated breath sample containing 755±7 ppbv ammonia within a sampling chamber volume of 128 ml was used. The samples were (a) applied to the sampling chamber 10 s before baseline completion, and (b) upon switching the valve were drawn across the electrode for 10 s (c) followed by switching to atmospheric air for 20 s, whereupon (d) the next sample entered the collection chamber (n=4).

Operation of the exemplary system is described as follows, initially with reference to FIGS. 3A, 3B and 3C. Approximately every 40 seconds, the samples are released by way of a chamber exhaust valve into a constant flow of ambient air. This vacuum flow provides control over the rate at which the samples are pulled across the electrode. Using a vacuum-based system has a large effect on decreasing the build up of water vapour from breath which provides similar results to the previous open environment studies. To know which vacuum flow would best decrease the humidity effects while providing quantifiable ammonia readings, a SUNON (Sunonwealth Electric Machine Industry Co., Ltd.) fan was tested. The fan was capable of working up to DC12 V and was tested at numerous flow rates. Adding simulated breath to the flow, observations from 90 to 128 L/min showed that higher flow rates decreased humidity effects, increased recovery of impedance, and increased ammonia sensitivity (FIG. 3A). A flow rate of 110.8±0.7 L/min was chosen since the humidity effect was sufficiently decreased and the ammonia signal was still easily isolated.

Figure 3B:
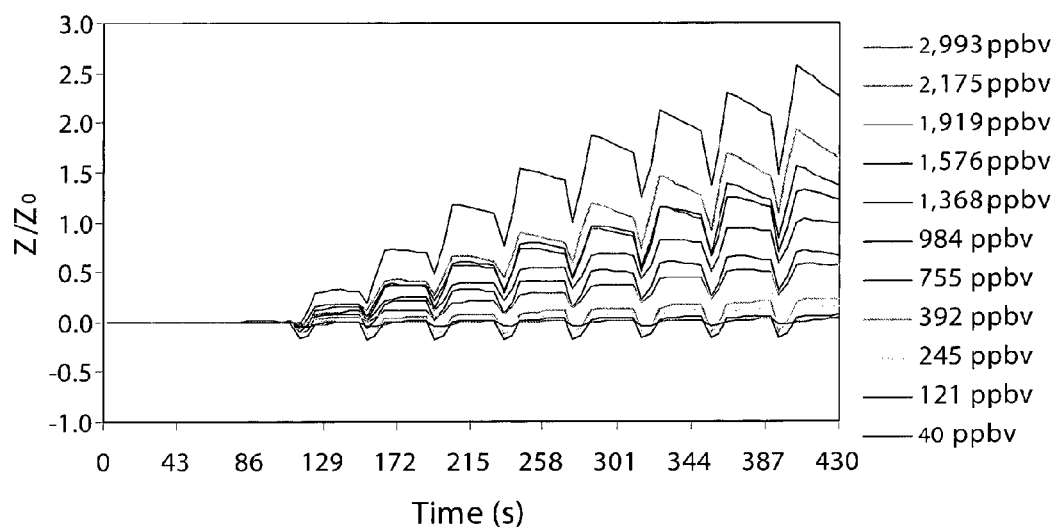
FIG. 3B. Calibration of simulated breath system in prototype device using a fan vacuum flow of 110.8±0.7 L/min. No exposure to the gas for 100 seconds formed the initial baseline. Beginning at time 101 s, two exhalations of four seconds each from the simulated breath system flowed into the chamber within a 10 second time frame. The chamber was then opened for 10 seconds via the chamber exhaust valve where the samples flowed onto the electrodes. This was repeated every 40 seconds until 430 seconds was reached.

With the vacuum system in place, breath measurements were taken using the prototype (FIG. 3B). Four second simulated breath samples were expelled into the prototype chamber two times within 10 seconds. With each exhalation, the excess breath that could not fit in the chamber was being forced out of passive valve number two. This took place every 40 seconds over a period of 430 seconds. After the 40 second increments, the chamber exhaust valve was opened and the trapped sample flowed across the electrode. Doing so allowed the breath samples (n=8) to generate impedance slopes unique to the individual ammonia concentrations. With the rate of exhalations and incremental pulls from the vacuum, there was no visible condensation build up within the chamber. Furthermore, the rapid response to ammonia concentrations showed that there may be potential for decrease in overall sampling time. Similar to the previous open environment trials, FIG. 3B displayed clear quantifiable ammonia measurements. It was also noticed that the outliers from humidity still existed, but were greatly reduced.

Figure 3C:
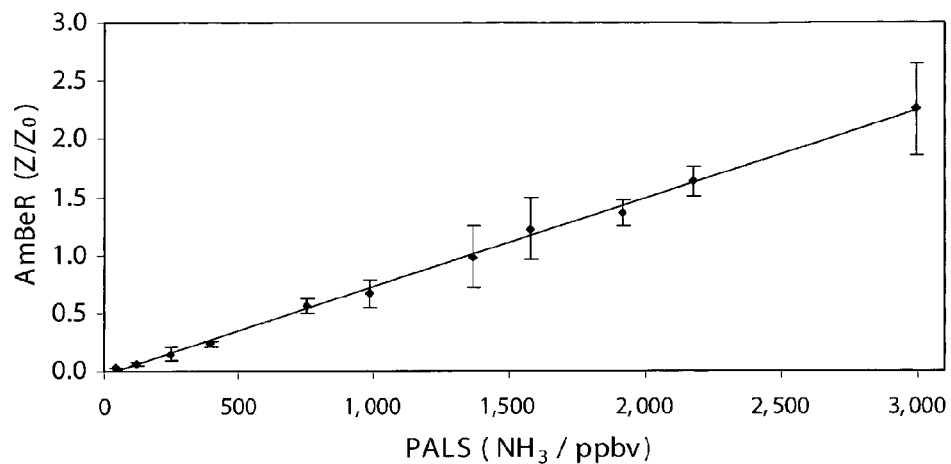
FIG. 3C. Relationship between ammonia concentration (as determined by PALS) and impedance response ($Z/Z_0$) after eight sequential breath samples using AmBeR ($R^2=0.99$, n=3). Slope=0.00076 $ppbv^{-1}$ and intercept=−0.0354.

The results of the eight breaths displayed within the 430 s of FIG. 3B are shown by way of the regression line in FIG. 3C. The response to ammonia is linear over the range of 40 to 2,993 ppbv.

TABLE 1

Data from FIG. 3a and FIG. 3b showing comparison of ammonia concentration against normalised impedance.

| *PALS ($NH_3$/ppbv, n = 5) | AmBeR ($Z/Z_0$, n = 3) | AmBeR ($Z/Z_0$, RSD %) |
|---|---|---|
| 40 ± 2 | 0.0318 ± 0.0027 | 8.4 |
| 121 ± 15 | 0.0641 ± 0.0155 | 24.1 |
| 245 ± 8 | 0.1490 ± 0.0554 | 37.2 |
| 392 ± 6 | 0.2372 ± 0.0228 | 9.6 |
| 755 ± 7 | 0.5553 ± 0.0631 | 11.4 |
| 984 ± 21 | 0.6659 ± 0.1249 | 18.8 |
| 1,368 ± 11 | 0.9831 ± 0.2631 | 26.8 |
| 1,576 ± 7 | 1.2242 ± 0.2641 | 21.6 |
| 1,919 ± 20 | 1.3620 ± 0.1169 | 8.6 |
| 2,175 ± 26 | 1.6373 ± 0.1347 | 8.2 |
| 2,993 ± 10 | 2.2594 ± 0.3905 | 1.3 |

Polyaniline is categorised among its three levels of oxidation known as reduced-state leucoemeraldine, oxidised-state pernigranaline, and intermediate-state emeraldine. The emeraldine form can further be categorised into emeraldine salt or emeraldine base. Emeraldine salt is the conductive form due to its delocalised positive charge. When interaction takes place between analytes such as gaseous ammonia and protonated polyaniline, the polyaniline deprotonates to the base form and ammonium is generated. Since the emeraldine salt form has proven to be semi-conductive, one can take advantage of this characteristic by using impedance to monitor the process. Impedance, Z, (in units of ohms) can be thought of as the ratio between an applied sinusoidal voltage, V, and a responding sinusoidal current, I:

$$Z = V/I \qquad (1)$$

Graphically, impedance is often represented as either a Complex-plane (e.g. Nyquist plot) or Bode plot, and is defined as a product of resistance, R, (in units of ohms) to current flow and capacitance, C (in units of farads):

$$|Z| = \sqrt{R + (1/\omega C)^2} \qquad (2)$$

$$|Z| = \sqrt{R + (1/\omega C)^2} \qquad (2)$$

where $\omega$ is the angular frequency in units of radians per second. When this formula is converted for Complex-plane plots, resistance is denoted as the "real" component, Z', of the x-axis while the capacitance makes up the "imaginary" element, Z", of the y-axis:

$$|Z| = \sqrt{(Z')^2 + (Z'')^2} \qquad (3)$$

Observing the relationship between the "in-phase" x-axis and "out-of-phase" y-axis also provides information on phase angle, $\phi$ (in units of degree) which is a helpful indicator of how far the angle of current has shifted away from the voltage. Hence, the impedance's phase angle $$\phi = 1/\omega RC \qquad (4)$$

could provide additional information about the changes being caused by interaction of an analyte such as ammonia gas with the conducting polymer. Bode plots differ from Complex-plane in that they display impedance magnitude and changes in phase as a logarithmic relationship against frequency.

By maintaining a static frequency, the changes in magnitude and phase can simply be monitored over an interval of time. The present specification provides a method that combines polyaniline-based electrodes and impedance configured to and capable of isolating an ammonia gas signal from the surrounding interferents of human breath. The reaction that is expected to take place when gaseous ammonia interacts with the nanoPANI on the electrodes is:

$$1PAH^+DBSA^- + NH_3 \rightleftharpoons 1PA + 1DBSA^-NH_4^+ \quad (5)$$

where $PAH^+$ is protonated (emeraldine) nanoPANI, PA is deprotonated (emeraldine) nanoPANI, $NH_3$ is gaseous ammonia, and $NH_4^+$ is ammonium Dodecylbenzene sulfonic acid, $DBSA^-$, provides the counter ion to balance the exchange of protons between nanoPANI and ammonia. As ammonia binds to nanoPANI, the available protonated sites decrease. This deprotonation causes a perturbation in the electrochemical signal that is directly proportional to the concentration of ammonia.

Figure 4:
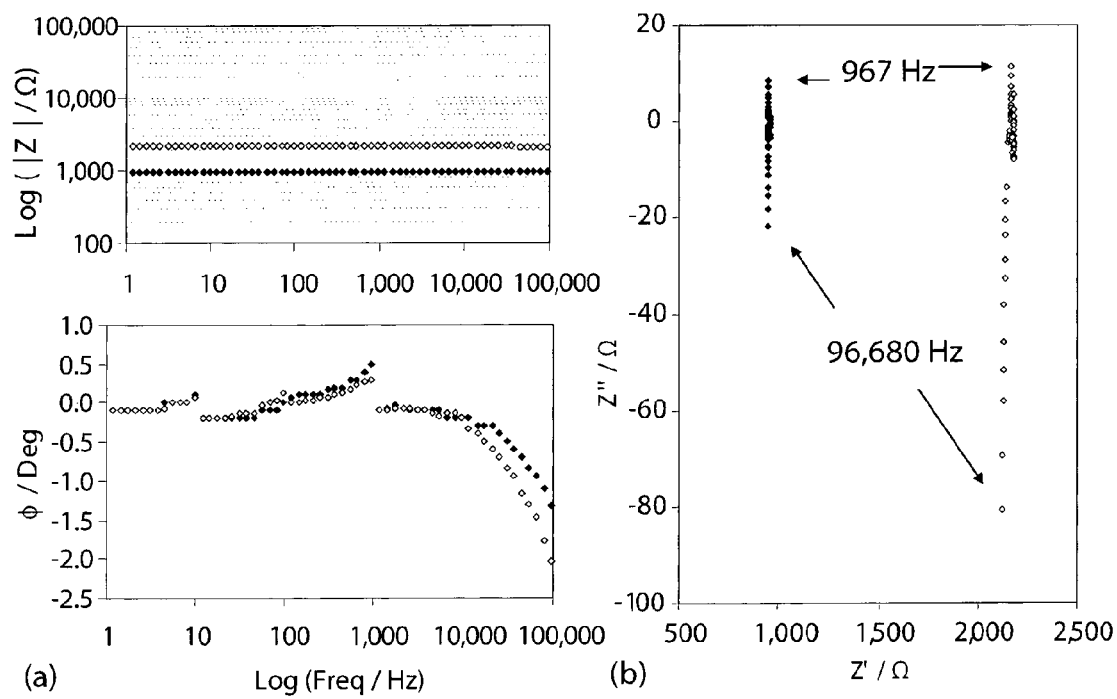
FIG. 4. Impedimetric and phase behaviour of electrode before (filled diamonds) and after (empty diamonds) exposure to 25 ppm ammonia. Results over the frequency range of 1 to 100,000 Hz were indicated by (a) Bode and (b) Nyquist plots.

Referring to FIG. 4, the capacitive and resistive effects were observed over a range from 1 to 100,000 Hz for Electrode Characterization. Bode plot data indicated that there was no significant change (955±1.33Ω; n=3) in mean absolute impedance, |Z|, over the range of frequencies when no ammonia exposure took place (FIG. 4a). However, a noticeable capacitive effect did arise once the frequency surpassed 962 Hz. This was indicated by a slight decrease in impedance from 956 to 951Ω, and a negative change in phase by 1.8 degrees. Upon the same three electrodes, direct exposure of 25 ppm ammonia took place until a stable baseline was formed. Once stable, the frequency spectrum was recorded. The newly formed baseline displayed a higher mean |Z| and deviation than without ammonia (2,166±17.8Ω; n=3). As with the results without ammonia, a capacitive effect occurred after 962 Hz. The impedance decreased from 2,167 to 2,124Ω, and phase displayed a negative change of 2.3 degrees. Nyquist data showed that once a frequency of 967 Hz was reached, a negative capacitive effect occurred in the electrodes regardless of whether or not there was ammonia exposure (FIG. 5b). However, exposure to ammonia resulted in a larger negative capacitance as the frequency increased. The critical frequency of 962 Hz was used for analysis in subsequent measurements. A sample of 30 electrodes printed from the same nanoPANI solution, were examined for their baseline variability and drift. Measurements were taken over a 600 s period to reflect an adequate breath sampling period. To first observe pure resistor stability and drift among the electrodes, a baseline consisting of the entirety of 600 s was recorded for each while they lay exposed to the open laboratory environment. The overall baseline impedance consisted of 121 data points which were averaged to create the intra-variable mean resistance and drift of that electrode's baseline. The electrode baselines were recorded as the mean absolute, |Z|, impedance at 962 Hz of 121 measurements over 600 s and the drift was expressed as the deviation and coefficient of variation of this mean over that time period. Of the 30 electrodes, the mean baseline ranged from 815 to 2,401Ω with an inter-electrode baseline mean and standard deviation of 1,443.7Ω and 478.2Ω (rsd=33%). Over the 600 s, the intra-electrode drift varied from 1 to 33Ω (rsd of 0.05 to 1.67%). To compensate for the initial variation in baseline, 10 electrodes were analysed ratio-metrically based on their initial baseline impedance ($R_0$) and then exposed to simulated breath ammonia. Electrodes were repeatedly exposed to 4 s of simulated human breath (≥90% RH, 37±1° C., 62±0.67 L/min) containing 245±8 ppb ammonia as determined by photoacoustic laser spectroscopy, followed by a gap of 15 s and the difference between $R/R_0$ at 100 s and 600 s was evaluated which was determined to be 2.69±0.12 (rsd=4.46%, n=10). This suggested that the electrodes could be used without the need for extensive individual calibration other than initial ratio-metric baseline correction. Further measurements on the electrodes applied this methodology.

Figure 5:
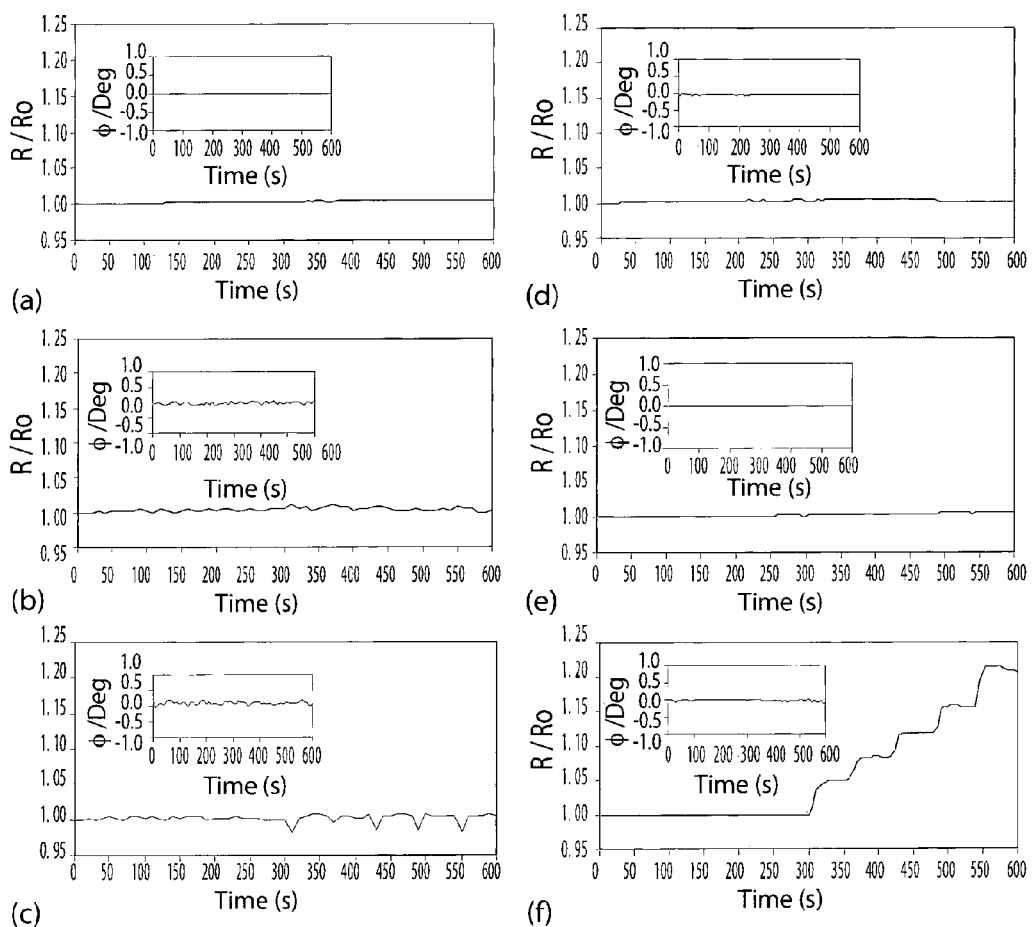
FIG. 5. Ratio-metric impedance and phase (inset) responses to potential interferent gases in human breath: (a) 99% carbon dioxide, (b) 99% nitrogen, (c) 99% oxygen, (d) 25 ppm hydrogen sulphide, (e) 25 ppm nitric oxide, (f) 25 ppm ammonia.
Figure 6:
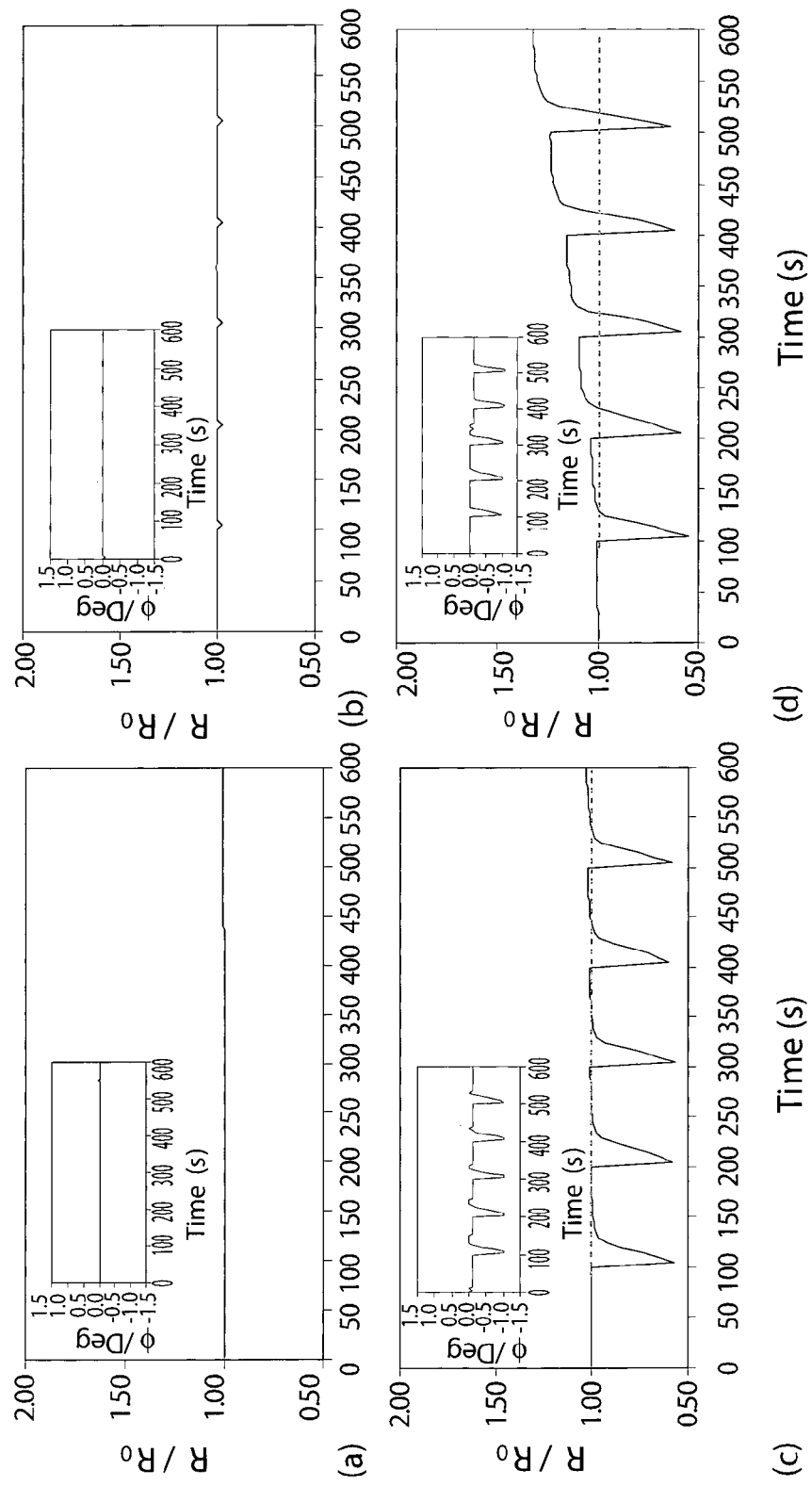
FIG. 6. Interdigitated nanoPANI electrode response of ratio-metric impedance, $R/R_0$, and inset phase angle, $\phi$, to (a) room temperature ambient air, 21±1° C., (b) warmed ambient air, 37±1° C., (c) warmed humidified ambient air, 37±1° C., ≥90% RH, and (d) warmed humidified air with ammonia, 37±1° C., ≥90% RH, 245±8 ppb.

Referring to FIG. 6, the Effect of Interferent Gases was evaluated. The gases were used at room temperature and contained no moisture. FIG. 5 shows direct exposure of the electrodes to a number of gases after 300 s of ambient exposure. Repeated exposure to concentrations of gas at 0.3 L/min flow rates for 4 s intervals were followed by a rest of 60 s. Carbon dioxide (99%), nitrogen (99%), oxygen (99%), hydrogen sulphide (25 ppm) and nitric oxide (25 ppm) showed no significant impedimetric or phase response from the electrodes, all at levels that were well above those that would be realistically found in a human breath sample. Ammonia (25 ppm) exhibited its well-established impedimetric response with a non-significant change in phase. From this, it was deduced that ammonia was the only major trace gas in breath that would have a significant effect on the nanoPANI electrodes. A comparison of water vapour would demonstrate another potential component. Referring to FIG. 6, the effect of Temperature, Humidity, and Humidified Ammonia, were evaluated. Tests were performed to evaluate the effects of ambient air at room temperature (21±1° C.), ambient air at human breath temperature (37±1° C.), humidified air at human breath temperature (37±1° C., ≥90% RH), and humidified air at human breath temperature containing ammonia (37±1° C., ≥90% RH, 245±8 ppb) on the ratio-metric impedimetric response of the nanoPANI-modified electrodes (FIG. 6). Over a time span of 600 s, the first 100 s were used as a baseline with no exposure. At 101 s, the electrodes were exposed to a sample for repeated periods of 4 s every 100 s. Exposure of ambient air (FIG. 6a) to the electrodes resulted in no significant change in ratio-metric impedance, $R/R_0$, or phase angle, φ. Heated ambient air (FIG. 6b) comparable to human breath temperature was detected by the sensor with a very negligible and transient response to $R/R_0$, but no observable change in φ. Heated humidified air (FIG. 6c) resulted in a significant transient decrease in $R/R_0$.

Furthermore, there was a noticeable negative phase shift that was directly proportional to this decrease indicating a capacitive effect due to water vapour. As the water evaporated from the electrode, the impedance and the phase both returned to their original baselines in a characteristic, time-dependent manner, following removal of the sample application to the sensor. In humidified air at human breath temperature containing ammonia (FIG. 6d), the interaction of humidity with the electrodes again caused a negative phase shift and an initial decrease in $R/R_0$, similar to FIG. 6c, despite the simultaneous interaction of ammonia. However, upon recovery of the electrode from temperature and humidity fluctuation, an increase in the $R/R_0$ baseline could be observed, whereas a non-significant change in the phase angle was apparent. The non-significant change in the phase angle indicated that ammonia inflicted a resistive effect on the electrodes, and the capacitive effects were specific to water vapour. In FIG. 6c, comparison of the "imaginary" capacitive data, Z", against the phase degree, φ, had a correlation of 0.9677. A similar correlation ($r^2$=0.9675) held true for sample 4 as well. This would imply that by calculating the phase angle as zero, the capacitance, and hence, the water vapour effects could be removed from the equation which would provide a real-time resistance signal specific to ammonia. This suggested that the impedimetric response signature of ammonia on the electrodes could be differentiated from temperature and humidity components by time-dependent control of the sampling methodology, or through differential analysis of the changes in impedance and phase. For the present work, a time-controlled breath sampling method was employed.

Figure 7:
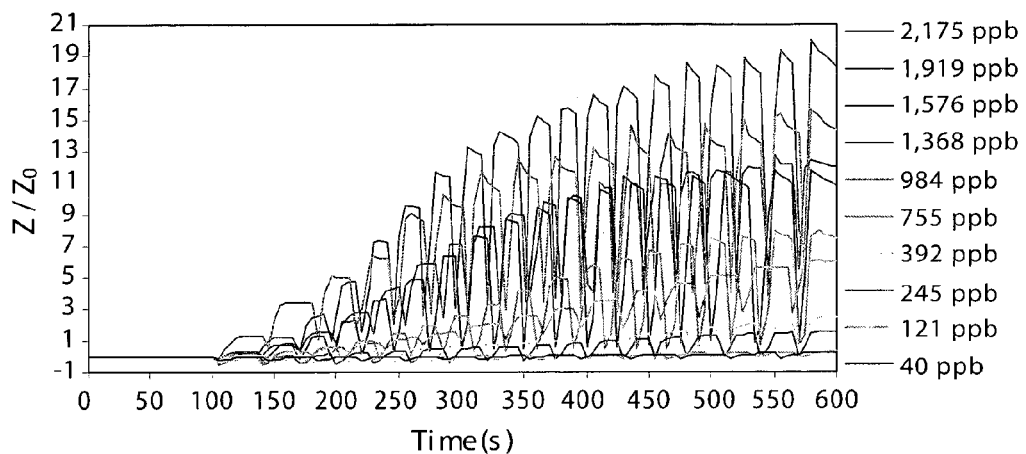
FIG. 7. Ratio-metric impedance response ($Z/Z_0$) profile of simulated breath samples on nanoPANI electrode measured at 962 Hz. No exposure to the gas for 100 s formed the initial baseline. Beginning at 101 s, a 62±0.67 L/min exhalation of four seconds from the simulated breath system flowed onto the electrode. This was repeated after the combined 15 s decrease in $Z/Z_0$ due to humidity and 15 s post-peak stabilisation resulting in approximately one breath measurement every 30 s until 600 s was reached.
Figure 8:
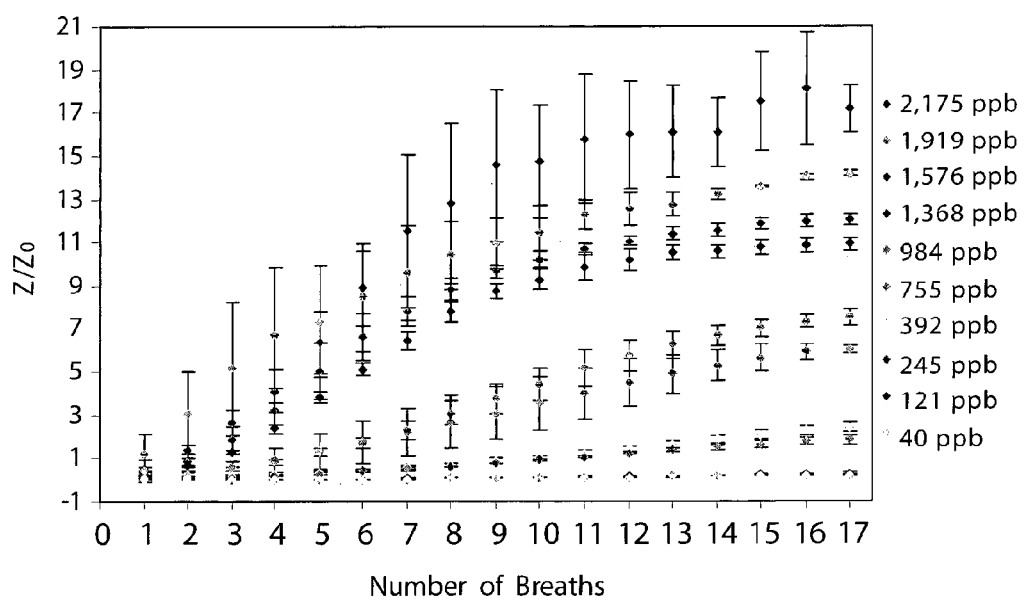
FIG. 8. Change in $Z/Z_0$ observed on nanoPANI electrodes (n=3) for each ammonia concentration at 30 s increments where breath one was at 130 s and breath 17 was from the post-peak stabilisation at 600 s.
Figure 9:
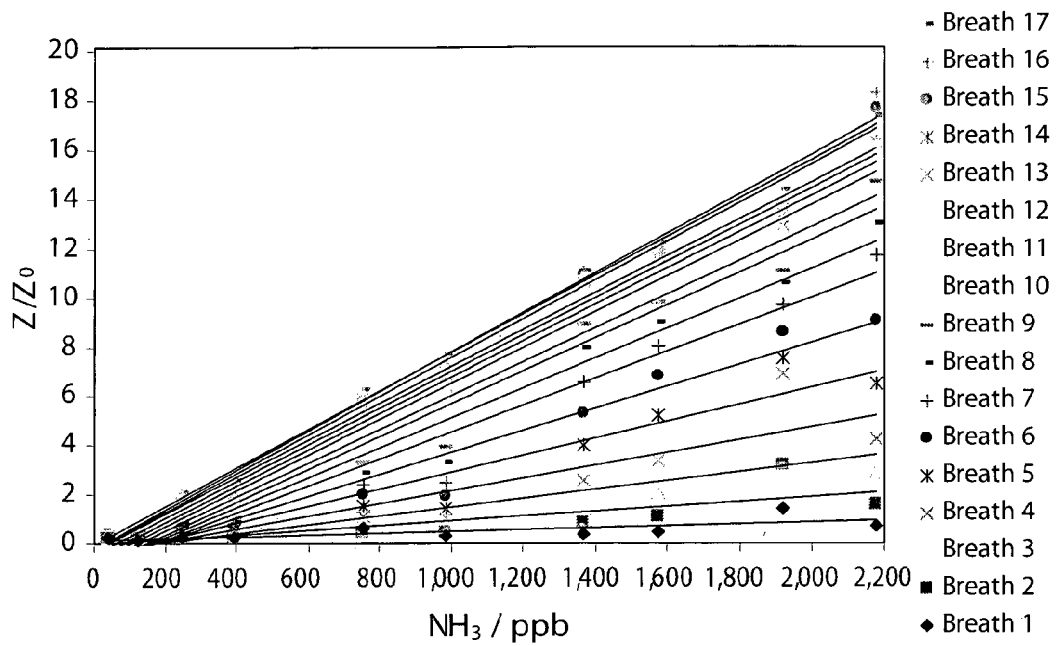
FIG. 9. Relationship between the impedance response ratio ($Z/Z_0$) and simulated breath ammonia concentrations demonstrating an increase in linearity with increased sample number.

Referring to FIGS. 7 to 9, Ammonia in Simulated Human Breath was quantified. NanoPANI electrodes were exposed to simulated breath samples (≥90% RH, 37±1° C., 62±0.67 L/min) containing ammonia at concentrations from 40±2 ppbv to 2,175±26 ppbv (n=3). Electrodes were repeatedly exposed to 4 s intervals of sample breath gas, followed by a 15 s delay over a 600 s period (FIG. 7). Again, the characteristic response from temperature and humidity on decreasing the |Z| was seen followed by recovery of the electrode upon return to ambient conditions. During this period, there was a cumulative response from the ammonia. Thus, after a specified number of breaths at controlled flow rate (and sample volume), the change in |Z| reached a level which was related to the ammonia concentration.

Peak responses were extracted from FIG. 7 after each simulated breath and plotted to determine the effect of sampling time/breath number on assay range and linearity (FIG. 8). A curve of the slope was calculated for each ammonia concentration and the changes in |Z| were observed at every 50 s increment.

Calibration curves obtained every breath from breath 1 to breath 17 are shown in FIG. 9. The response was found to be linear across the full assay range tested from 40±2 ppbv to 2,175±26 ppbv ammonia. However, the correlation between ammonia concentration and |Z| improved with respect to increased breath number. The correlation coefficient was found to be 0.56 at breath 1, but showed improvement by breath 17 with a correlation of 0.99. Furthermore, it had a slope and intercept of 0.0079 ppbv$^{-1}$ and 0.28, respectively, and the rsd of the replicates varied between 3% to 11% (n=3). Based on this data and the intra-electrode baseline drift variability determined earlier, a theoretical LOD of approx. 6.3 ppb could be determined (S/N=3).

Figure 10:
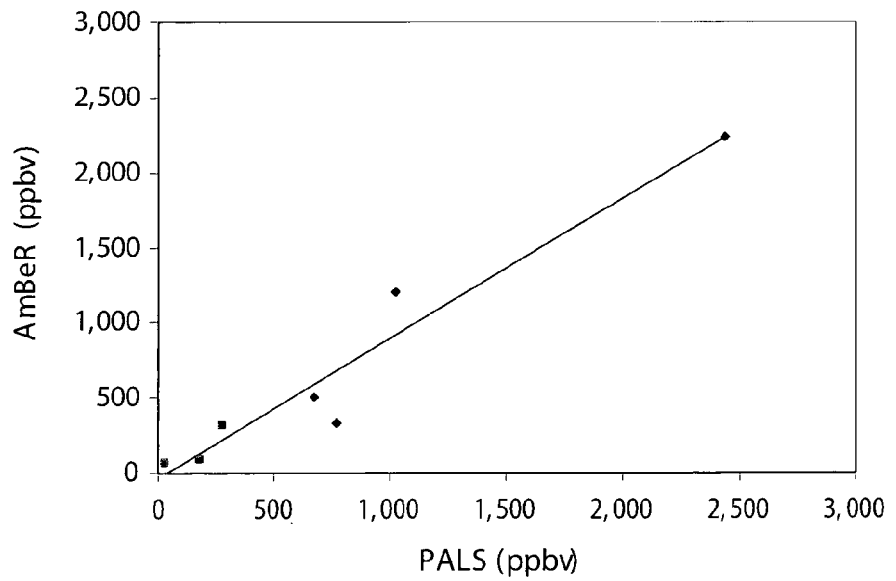
FIG. 10 Pre-dialysis (blue diamond) and post-dialysis (red square) breath ammonia concentrations measured using AmBeR and PALS (n=7). The progression displayed a slope and intercept of 0.9287 ppbv and −39.73 ppbv, respectively (r=0.97, p<0.01).

Referring to the Figures, an exemplary system for sensing and measuring ammonia in a breath sample according to the present specification was also tested in a clinical setting and exemplary results are noted below. Correlation of breath ammonia concentrations between system for sensing and measuring ammonia in a breath sample and PALS (Photoacoustic Laser Spectroscopy which is a high end, instrumental method of measuring ammonia in breath) Eight breath ammonia samples were taken using PALS immediately followed by system for sensing and measuring ammonia according to the specification) (AmBeR). Four samples were pre-dialysis and four were post-dialysis (Table 5 and FIG. 10). This yielded a Pearson correlation coefficient of 0.97 (p<0.01). With a slope and intercept of 0.9287 ppbv and −39.73 ppbv, respectively there was a slight bias for PALS. This could be an indication that the PALS device is sensitive to unknown metabolites of which AmBeR is not, and showing the specificity of AmBeR to ammonia. Hence, further clinical analysis was performed with the AmBeR device.

TABLE 2

Pre-dialysis (n = 4) and post-dialysis (n = 3) breath ammonia concentrations obtained from four haemodialysis patients using both AmBeR and PALS (n = 7). Negative values are indicated by (—).

| Volunteer (number) | Dialysis (Pre/Post) | PALS (ppbv) | AmBeR (ppbv) |
|---|---|---|---|
| 1 | Pre | 1,030 | 1,203 |
|   | Post | 16 | — |
| 2 | Pre | 2,442 | 2,230 |
|   | Post | 39 | 72 |
| 3 | Pre | 774 | 335 |
|   | Post | 186 | 98 |
| 4 | Pre | 678 | 506 |
|   | Post | 282 | 322 |

Figure 11:
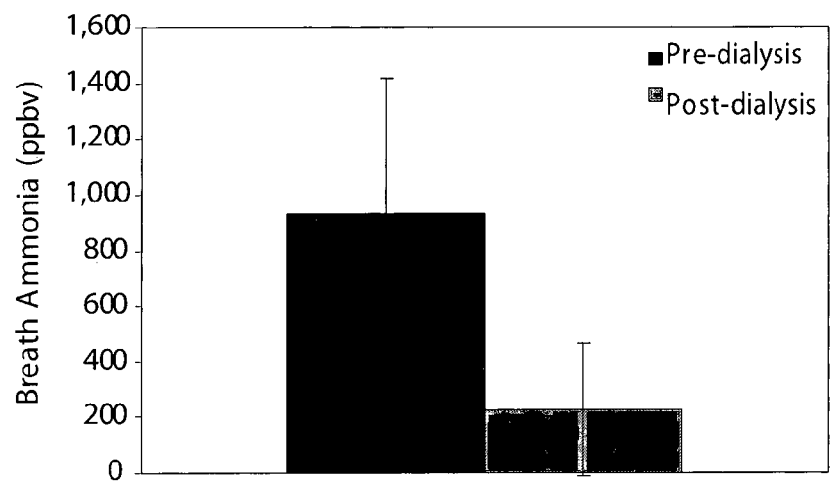
FIG. 11 The mean pre-dialysis (930±483 ppbv, n=51) and post-dialysis (227±236 ppbv, n=45) breath ammonia measurements in the haemodialysis population (p<0.05) as determined by the AmBeR system.

Result data based on device testing are provided. Pre- and post-dialysis measurements of breath ammonia, blood urea nitrogen, and blood creatinine in the haemodialysis patient cohort. The breath ammonia levels measured using AmBeR along with blood urea nitrogen, blood creatinine, corresponding reduction ratios, and Kt/V values from all 51 volunteer samples are compiled in Table 2. The observed patient cohort (n=20) had a mean age of 63 years (ranged 36 to 91 years). There were ten female and ten male volunteers. The mean body mass index was 25.79 kg/m$^2$ (ranged 17.58 to 32.42 kg/m$^2$). Of these patients, 11 were willing to perform repeated correlative measurements of breath ammonia and blood nitrogen resulting in a complete sample count of 51. Reductions in breath ammonia, blood urea nitrogen, and blood creatinine concentrations were observed in all patient samples following dialysis. Referring to FIG. 11 Pre- and post-dialysis measurements of breath ammonia in the haemodialysis patient cohort. Breath ammonia measurements had a pre-dialysis population mean of 930±483 ppbv (ranged 164 to 2,243 ppbv, n=51) and a post-dialysis mean of 227±236 ppbv (ranged 19 to 1,138 ppbv, n=45). FIG. 11 represents the difference between pre- and post-dialysis breath ammonia measurements demonstrating the link between blood and breath metabolites. SPSS analysis of the correlation between the two-data sets generated a two-tailed p<0.05 displaying a high level of significance in the difference between pre- and post-dialysis measurements.

Figure 12:
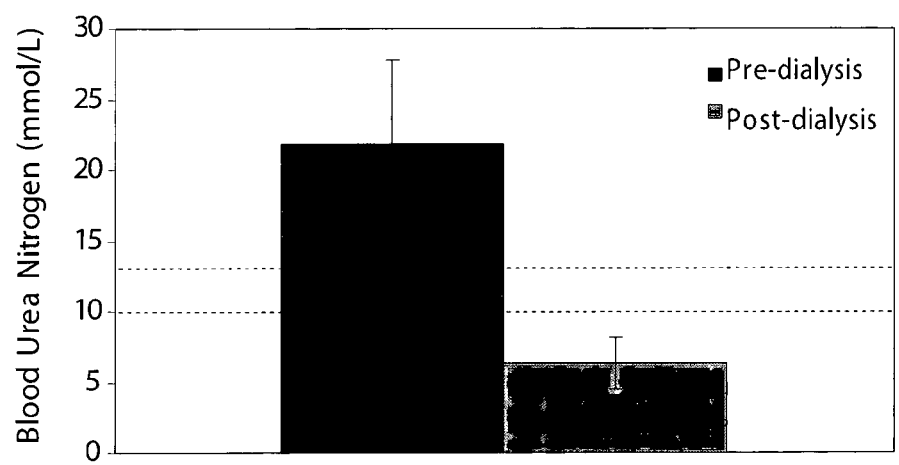
FIG. 12 The mean pre-dialysis (22±6 mmol/L) and post-dialysis (6±2 mmol/L) blood urea nitrogen measurements in the haemodialysis population (ρ<0.01, n=51). Dashed lines designate the approximate range (10 to 13.2 mmol/L) indicative of renal failure.
Figure 14:
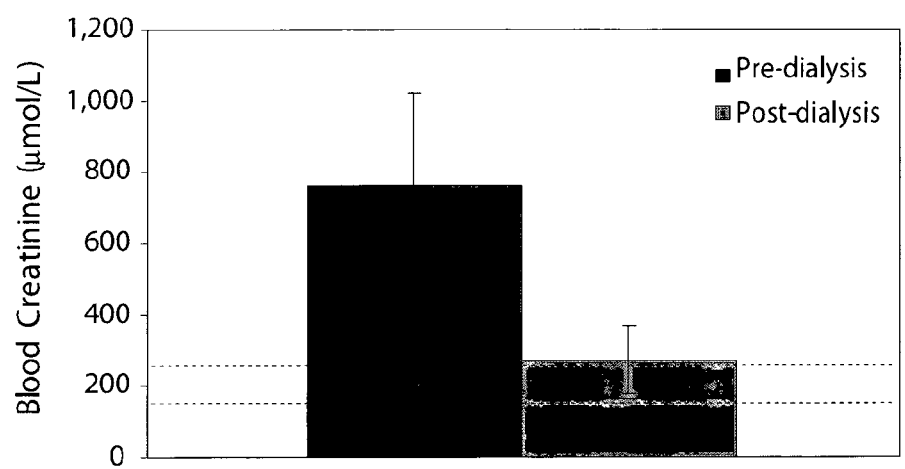
FIG. 14 The mean pre-dialysis (764±261 μmol/L) and post-dialysis (302±96 μmol/L) blood creatinine measurements in the haemodialysis population (p<0.01, n=51). Dashed lines designate the approximate range (141 to 250 μmol/L) indicative of renal failure.

Referring to FIG. 12, Pre- and post-dialysis measurements of blood urea nitrogen in the haemodialysis patient cohort are shown. Both breath ammonia and blood urea nitrogen concentrations were found to decrease from pre- to post-dialysis. Blood urea nitrogen pre-dialysis had a mean of 22±6 mmol/L (range of 9 to 35 mmol/L), and reduced to a mean of 6±2 mmol/L (range of 3 to 10 mmol/L) in post-dialysis measurements (FIG. 12). Analysis of this difference using a paired t-test displayed a t-statistic of 23.00 (two-tailed, p<0.01). The relationship between the absolute concentrations of breath ammonia and blood urea nitrogen was studied. This was found to have a Pearson correlation coefficient of 0.61 (p<0.01, n=96) (FIG. 14). The correlation r=0.61 is not very strong, but the strength of significance, p<0.01, among the measurements demonstrates enough potential for continued assessment in clinical applications to take place.

Figure 13:
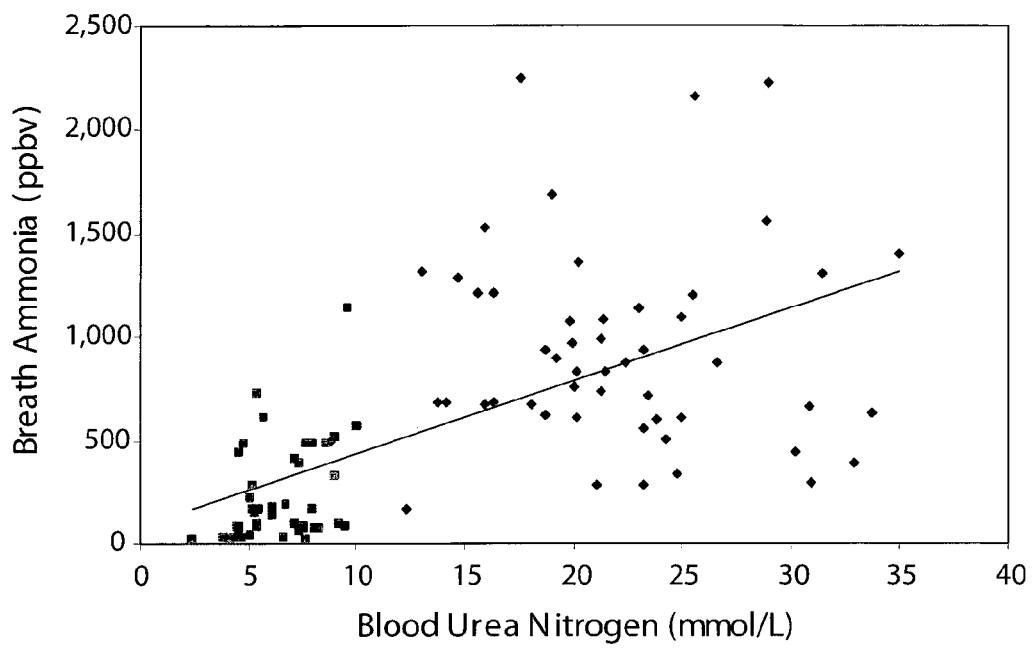
FIG. 13 Pre-dialysis (blue diamond) and post-dialysis (red square) of absolute breath ammonia and blood urea nitrogen concentrations (n=96). The regression displayed a slope and intercept of 35.57 ppbv and 78.56 ppbv, respectively, with r=0.61 (ρ<0.01).
Figure 15:
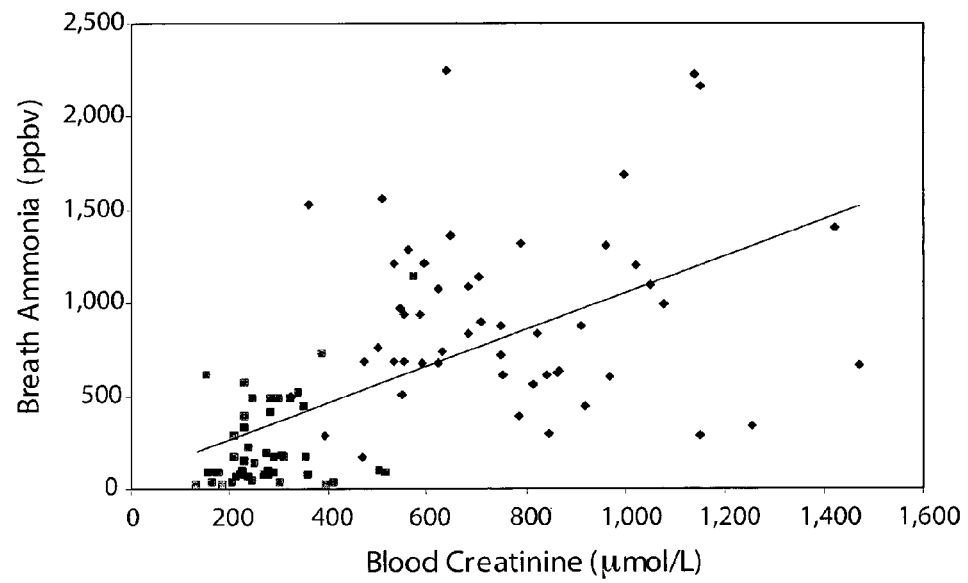
FIG. 15 Pre-dialysis (blue diamond) and post-dialysis (red square) of breath ammonia and blood creatinine levels using the device (n=96). The progression displayed a slope and intercept of 0.9895 ppbv and 68.70 ppbv, respectively, with r=0.60 (p<0.01).

Referring to FIG. 13 Pre- and post-dialysis measurements of blood creatinine in the haemodialysis patient cohort data are described. Pre-dialysis measurements of blood creatinine had a mean of 764±261 µmol/L (ranged from 325 to 1,470 µmol/L) and a post-dialysis concentration mean of 302±96 µmol/L (ranged from 133 to 576 µmol/L) (FIG. 13). As with the blood urea nitrogen measurements, the observed patients had pre-dialysis blood creatinine means that were higher than the values indicated for renal failure. However, the post-dialysis mean was marginally above the cut-off for normal creatinine. Analysis of these two means using a paired t-test yielded a t-statistic of 18.58, and a two-tailed $p<0.01$ demonstrating a significant difference between the pre- and post-dialysis creatinine levels. The relationship between the absolute concentrations of breath ammonia and blood creatinine had a Pearson correlation coefficient of 0.60 ($p<0.01$, $n=96$) (FIG. 15) which was very similar to the 0.61 value previously determined with blood urea nitrogen.

Figure 16:
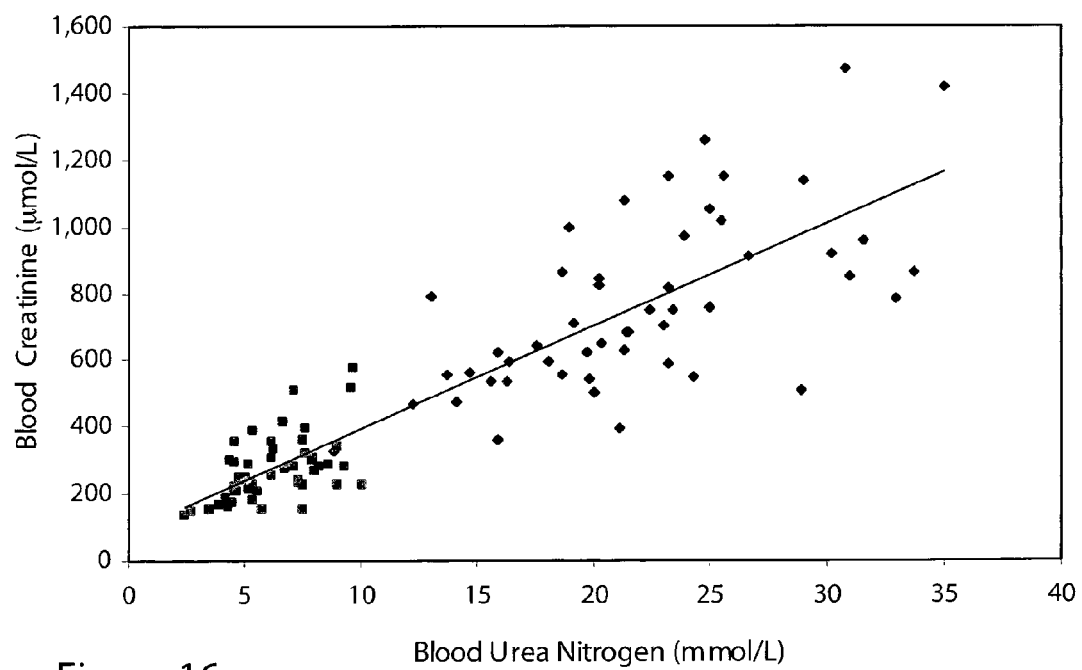
FIG. 16 Pre-dialysis (blue diamond) and post-dialysis (red square) of blood creatinine and blood urea nitrogen concentrations (n=102). The regression displayed a slope and intercept of 30.82 µmol/mmol/L and 83.56 µmol/L, respectively, r=0.88 (p<0.01).

Referring to FIG. 16, a Comparison of pre- and post-dialysis measurements of blood urea and blood creatinine in the haemodialysis patient cohort data are described. The laboratory results for absolute blood urea and creatinine were compared with one another to see if there was a relationship between these two blood nitrogen species (FIG. 16). This yielded a Pearson correlation of 0.88 ($p<0.01$) demonstrating a strong relationship.

Figure 17:
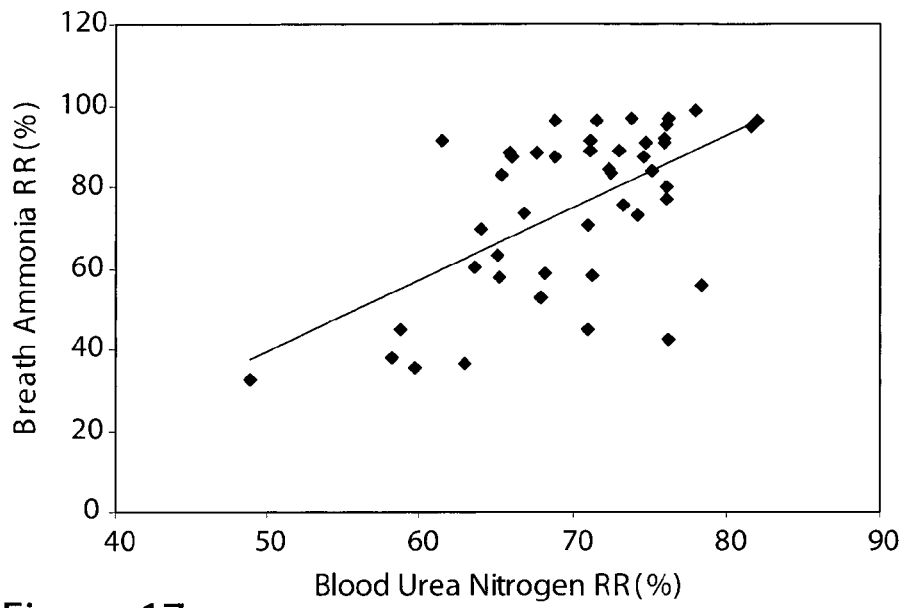
FIG. 17 Relationship of breath ammonia and blood urea reduction ratios for the haemodialysis patient population (r=0.60, p<0.01, n=45).
Figure 18:
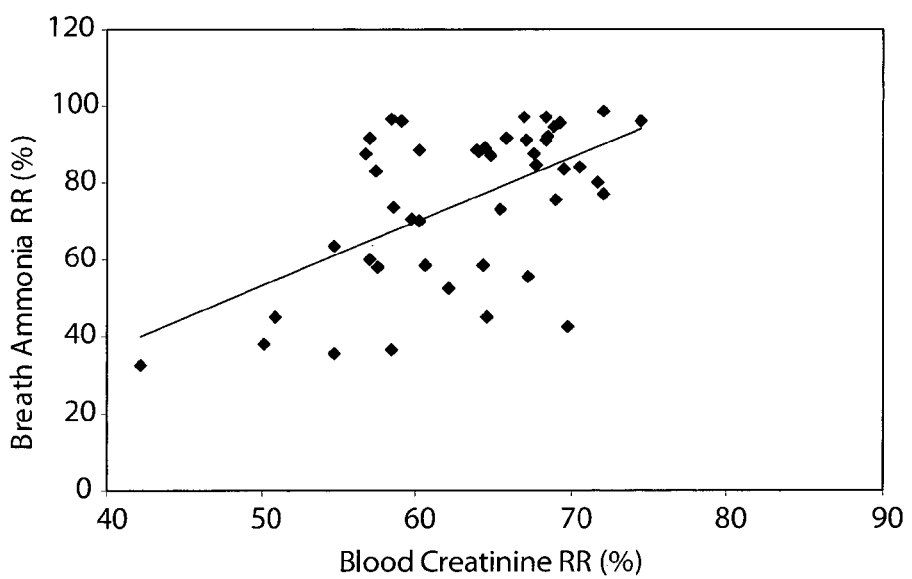
FIG. 18 Relationship of breath ammonia and blood creatinine reduction ratios for the haemodialysis patient population (r=0.55, p<0.01, n=45).

Referring to FIGS. 17 and 18 Correlation of breath ammonia reduction ratios with blood urea and blood creatinine reduction ratios in the haemodialysis patient population data are discussed. The population data established in FIGS. 17 and 18 did not yield very strong correlations between breath ammonia and either blood urea nitrogen or creatinine. It has already been discussed that additional patient-specific variables may make it difficult to establish a strong population correlation. Thus, other approaches were investigated to see whether better relationships could be established between breath ammonia and blood nitrogen levels that could eliminate such subject-specific variables. One approach to this was to investigate reduction ratios in breath ammonia, urea, and creatinine as such ratios only take into account the overall change in levels pre- and post-dialysis, rather than the absolute concentrations. However, the relationship between the reduction ratios from pre- to post-dialysis breath ammonia and blood urea concentrations yielded a Pearson correlation coefficient of 0.60 ($p<0.01$, $n=45$) (FIG. 17).

Figure 19:
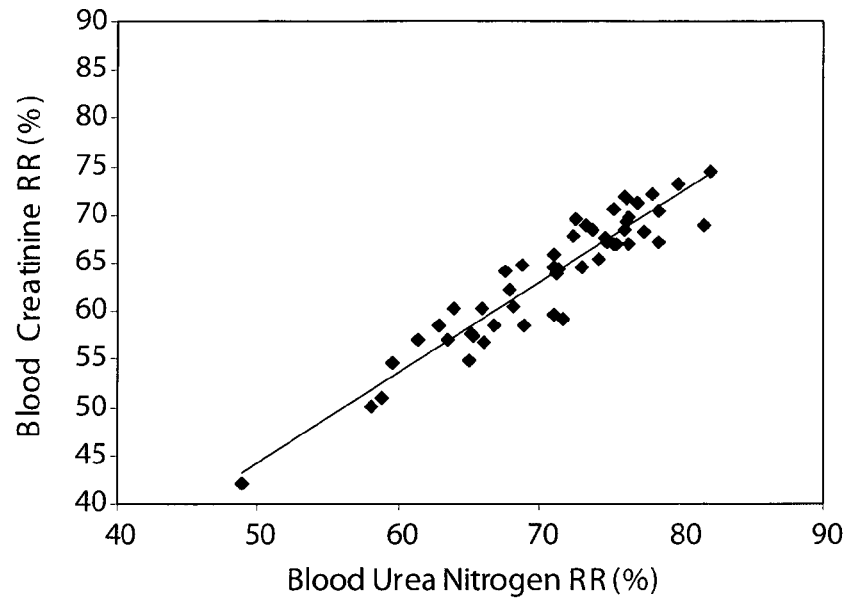
FIG. 19 Relationship of blood creatinine reduction ratios and blood urea nitrogen reduction ratios for the haemodialysis patient population (r=0.94, p<0.01, n=51).
Figure 20:
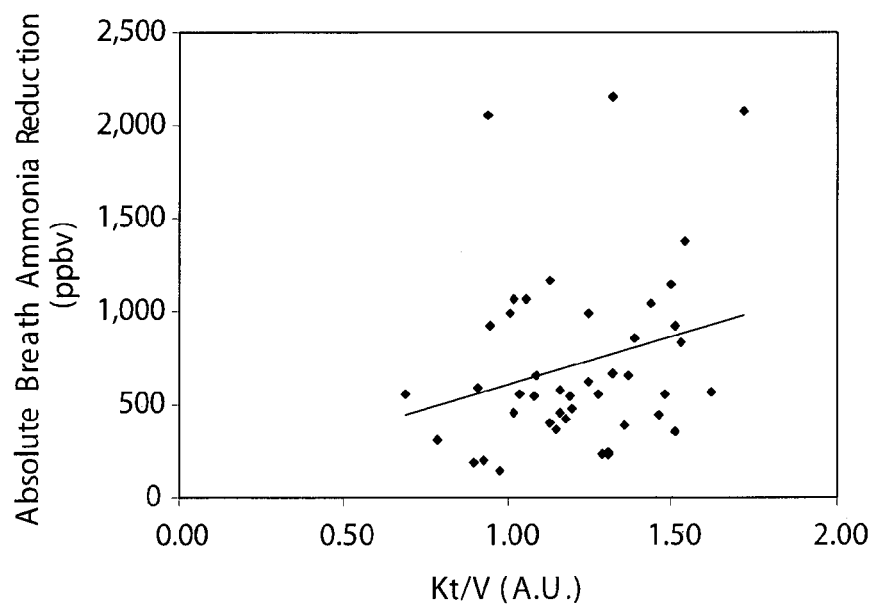
FIG. 20 Relationship between absolute breath ammonia reduction and Kt/V for the haemodialysis patient population samples (r=0.25, p=0.102, n=44).
Figure 21:
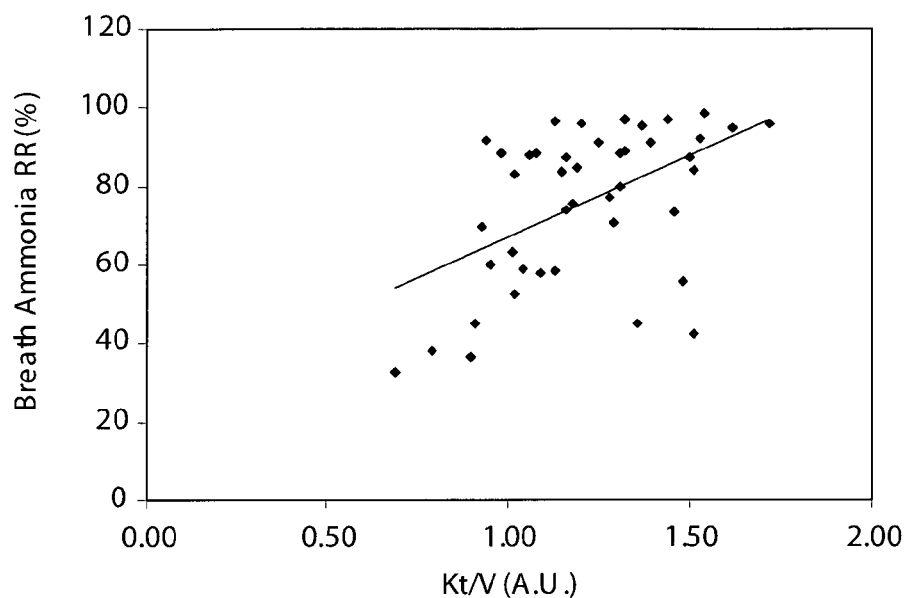
FIG. 21 Relationship between breath ammonia reduction ratio and Kt/V for the haemodialysis patient population samples (r=0.50, p<0.01, n=44).
Figure 22:
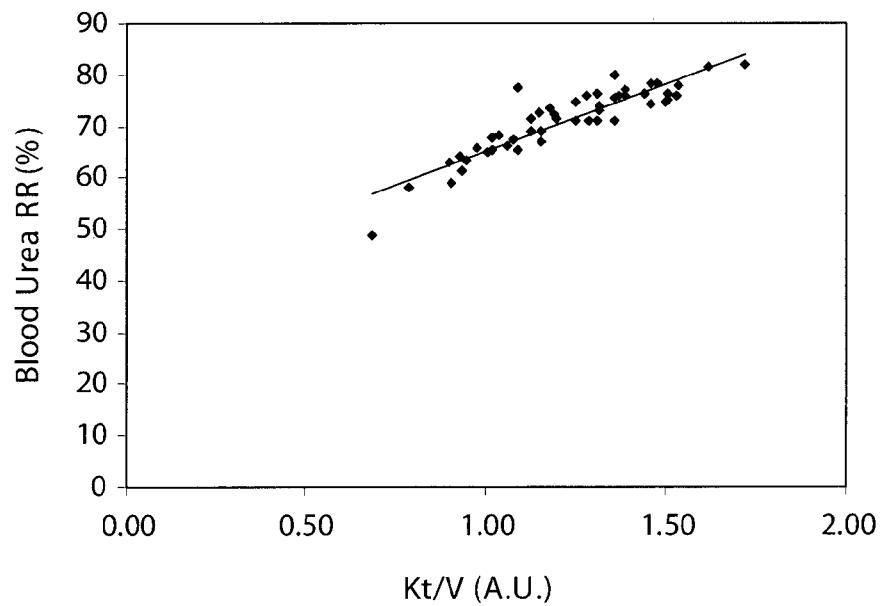
FIG. 22 Relationship between blood urea nitrogen reduction ratio and Kt/V for the haemodialysis patient population samples (r=0.93, p<0.01, n=44).

The relationship between the reduction ratios from pre- to post-dialysis breath ammonia and blood creatinine concentrations had a Pearson correlation coefficient of 0.55 ($p<0.01$) (FIG. 18). This was a slightly lower correlation in comparison to the previously observed urea reduction ratio ($r=0.60$). The relationship between the reduction ratios from pre- to post-dialysis blood creatinine and urea concentrations had a Pearson correlation coefficient of 0.94 ($p<0.01$) (FIG. 19) showing the strong link between the blood nitrogen species and the consistency from one patient to the next. However, it is worth noting that the range observed is indicative of individual metabolic behaviour. In other words, each patient has a reduction ratio that was unique to themselves and varied from levels in excess of 85% to levels lower than 45%. Referring to FIGS. 20 to 22 data showing the Relationship between Kt/V and absolute breath ammonia reduction, breath ammonia reduction ratio, and blood urea nitrogen reduction ratios in the haemodialysis patient population is discussed. The correlation between the absolute breath ammonia reduction and Kt/V of 44 patient samples (only 44 of the 51 patient samples could be measured due to lack of post-dialysis breath ammonia measurements for 6 patients, and no haematocrit data for one patient) displayed a Pearson correlation coefficient of 0.25, and was not significant ($p=0.102$) (FIG. 20), indicating that use of Kt/V to correlate with absolute breath ammonia reduction would not be beneficial. Breath ammonia reduction ratios of the 44 patient samples displayed a Pearson correlation of 0.50 ($p<0.01$) with Kt/V indicating a stronger relationship (FIG. 20). The relationship between Kt/V and blood urea reduction ratio yielded a Pearson correlation coefficient of 0.93 ($p<0.01$) (FIG. 22). This correlation was significantly higher than between the Kt/V and absolute breath ammonia reduction ($r=0.25$) and breath ammonia reduction ratio ($r=0.50$) indicating that use of Kt/V to correlate with blood urea reduction ratios would be useful.

The relationship between the absolute concentrations of breath ammonia and blood urea nitrogen are shown in FIG. 23. It can be seen that the correlation between breath ammonia and blood urea nitrogen ranged from 0.82 to 0.96 with p-values of <0.01 and <0.05, indicating strong correlation and good statistical significance in all cases. The fact that the correlations for all intra-individual data were strong with good statistical significance suggests that the relationship between breath ammonia and blood urea levels remain reasonably consistent between dialysis sessions for a particular individual and so the correlation is not utterly dependent on the dynamics of a single dialysis event. It was also obvious that the relationship between breath ammonia and blood urea varied considerably from patient to patient as evidenced by the slopes (ranging from 15.70 to 122.59 ppbv).

Furthermore, the relationship between breath ammonia and blood urea appears to be reasonably linear for each individual. All these facts suggest that there would appear to be a defined relationship between breath ammonia and blood urea nitrogen levels that was specific to each individual. The reasons for this specific relationship are, as yet, undetermined, but again probably relate to patient-specific factors. For example, Volunteer 8 (FIG. 23 $h$) yielded pre-dialysis urea concentrations in excess of 30 mmol/L, while only registering ammonia levels of approximately 440 ppbv, and Volunteer 10 (FIG. 47 $j$) had a pre-dialysis breath ammonia level of 2,243 ppbv with a urea level of 17.6 mmol/L. This is an obvious display of the unique physiological factors associated with each individual.

Referring to FIG. 24 Intra-individual correlations of breath ammonia and blood creatinine levels. The relationship between the absolute concentrations of breath ammonia and blood creatinine begins in FIG. 24. The correlation between breath ammonia and blood creatinine had a wider range than that with urea going from 0.71 to 0.97 with p-values of <0.01 and <0.05, once again displaying a strong correlation with good statistical significance. Volunteer 6 (FIG. 24 $f$), however, displayed a non-significant relationship ($p=0.074$) between breath ammonia and blood creatinine. The reason for this result is unidentified, but is likely the cause of an unknown interferent given that the other correlations were strong. As with the urea correlations, the good statistical significance among the intra-individual data suggests that the relationship between breath ammonia and blood creatinine levels remain reasonably consistent between dialysis sessions. In addition, the behaviour observed by the slopes (ranging from 0.47 to 2.64 ppbv) was similar to that seen with urea analysis where the relationship varied from person to person suggesting patient-specific factors are involved. The previously discussed Volunteer's 8 (FIG. 24 $h$) and 10 (FIG. 24 $j$) yielded pre-dialysis creatinine concentrations in excess of 500 μmol/L, yet Volunteer 8 only expressed breath ammonia concentrations of approximately 400 ppbv in this region while Volunteer 10 was over 900 ppbv on all accounts again demonstrating individual specificity.

Referring to FIG. 25 Intra-Individual Correlations of Blood Creatinine and Blood Urea Levels The relationship between the absolute concentrations of blood urea and creatinine begins in FIG. 25. The correlation between blood urea nitrogen and creatinine ranged from 0.90 to 1.00 with p-values of <0.01 and <0.05, indicating strong correlation and good statistical significance. The variation previously seen in the slopes also existed between blood urea and creatinine (ranging from 23.84 to 43.71 µmol/mmol/L), but not as much as between blood and breath. It is also worth noting that the relationship between blood urea and creatinine appears to be reasonably linear among the individuals suggesting that the relationship between blood urea nitrogen and creatinine levels displays similar behaviour from person to person. Although, slight variations do exist as exemplified by the previously mentioned Volunteer 8 (FIG. 25 h) yielded pre-dialysis urea concentrations in excess of 30 mmol/L, while registering creatinine levels of approximately 1,000 µmol/L, and Volunteer 10 (FIG. 25 j) had a pre-dialysis creatinine level close to 1,000 µmol/L where urea concentrations were only at approximately 20 mmol/L. By comparison to the population data, the improved correlations observed between breath ammonia, blood urea, and blood creatinine within individuals demonstrates a higher level of consistency among intra-individual samples. It is likely that the metabolic and physiological characteristics (e.g. kidney function, muscle mass, etc.) unique to the individuals would result in greater consistency in blood and breath measurement behaviour than would inter-individual comparisons among a population. This is demonstrated by the variations in individual slopes which signify metabolic behaviour unique to each person. In addition, the Pearson correlations found between breath ammonia and blood urea nitrogen were within a slightly smaller range than with blood creatinine suggesting that a more consistent and potentially stronger relationship may exist between breath ammonia and blood urea.

Referring to FIGS. 26 to 31 comparative data relating to the PTFE modified PANI sensors in aqueous environments is discussed. In order to assess the effects of the printed PTFE layers on sensor performance, modified and unmodified PANI sensors were tested with a variety of aqueous solutions. Two possible modalities can be employed when analysing solutions for dissolved gases: immersion and drop. Tests were initially conducted using full immersion of the sensors within solution, however the work detailed here involved small drops—simulating methods that may be employed for tests involving small volumes, such as blood. In each case, a 100 µL drop was placed on the working area of the sensor (as shown in FIG. 27d) and the response measured through impedance-time measurements.

Figure 26:
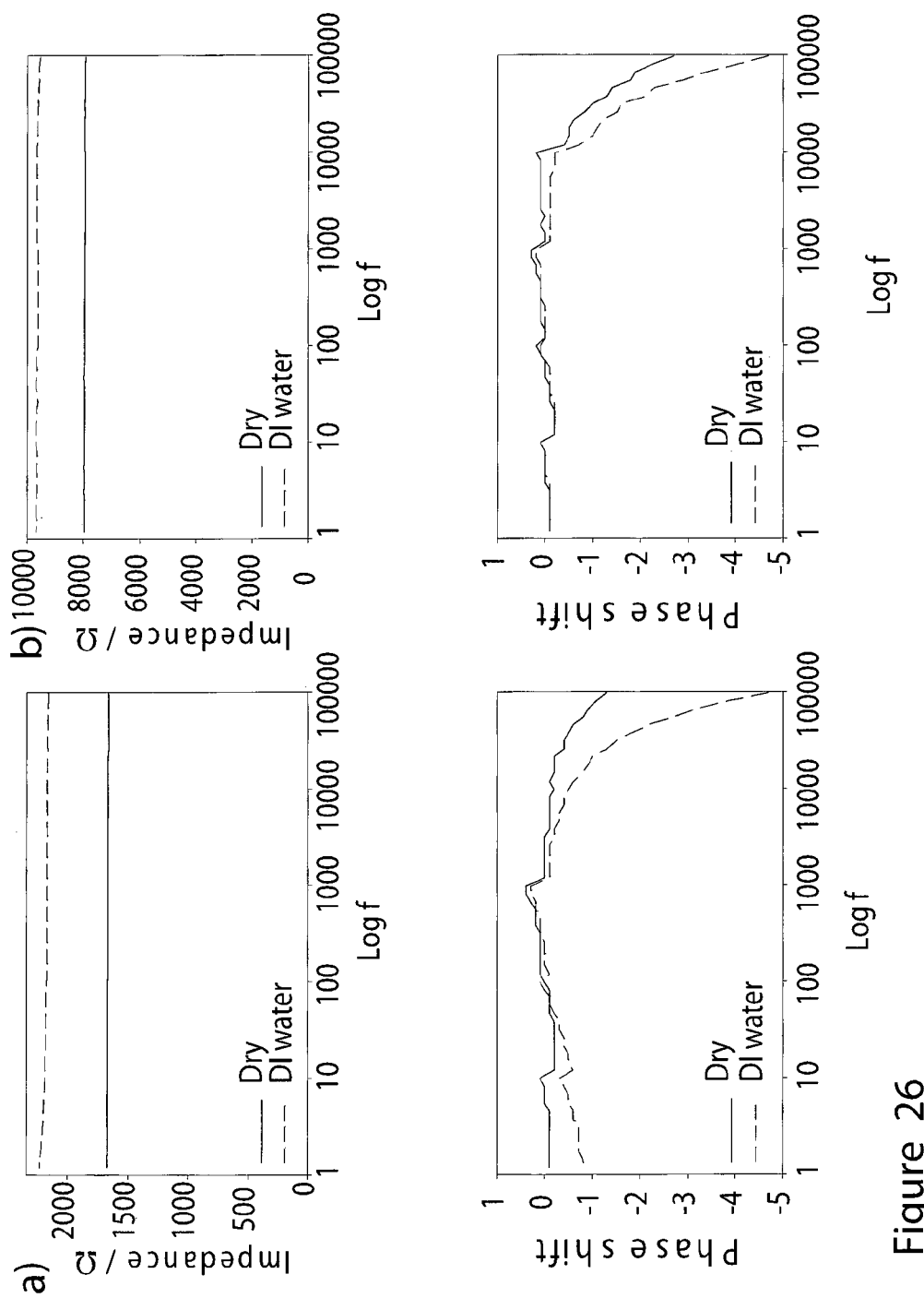
FIG. 26. Impedance spectra obtained for (a) an unmodified PANI sensor and (b) a PANI sensor modified with PTFE (12 layers at 10 µm). Bode plots: Upper graphs show impedance against frequency and lower plots show phase angle shift against frequency. Impedance parameters: $E_{init}$: 0V, $E_{amp}$: 5 mV FIG. 27. Impedance/time plots observed for (a) an unmodified PANI sensor and (b) a PANI-PTFE sensor to deionised water, 23.3% w/v NaCl in water and 50 ppm ammonia in water (100 µL droplets on sensor). Impedance parameters: $E_{init}$: 0V, $E_{amp}$: 5 mV, f=962 Hz, $t_{sample}$, =5 s.

FIG. 26 shows the impedance spectra (Bode plots) obtained for PANI and PANI-PTFE sensors under dry conditions and after a 100 µL drop of distilled, deionised water has been applied. In comparing the sensors under dry conditions, it can be seen that little variation in impedance is observed over a wide frequency range in both cases. The main point that can be taken from this data is the increase in impedance observed when a sensor is coated with PTFE—typically between 4 and 5 times the original baseline. This effect is reversible and is presumably due to deprotonation of the PANI during printing of the PTFE dispersion. Between 1 and 10 KHz, no significant deviation in phase angle is observed for either data—implying that both sensors are behaving as ideal resistors under these conditions. Above 10 KHz, a slight capacitive effect is observed as evidenced by a slight shift in the negative direction, with a slightly greater effect noticeable for the PANI-PTFE sensor. The impedance spectra obtained with the droplet of deionised water show an increase in impedance in both cases though no significant relative variation is observed for either sensor across the frequency range. The PTFE modified sensor shows little variation in phase angle on addition of the droplet (only a slight increase at the high end) however the unmodified sensor displays observable shifts at both the high and low (>100 Hz) range. In order to minimise the effect of water both the impedance and phase angle, the optimum impedance frequency would be between 100 and 10 KHz. Therefore, for studies involving impedance/time measurements, a fixed frequency of 1000 Hz was set (for which the CHI potentiostat applied 962 Hz). These variations were observed with application of distilled, deionised water (18 MΩ) where ionic conduction effects would be at a minimum. To determine the effect of more conductive solutions, further studies were performed with additional aqueous samples to give a wider assessment of the PTFE modification.

FIG. 27 shows the effects of three different aqueous samples on each of the sensors; distilled, deionised water as before and 23.3% w/v NaCl and 50 ppm ammonia, both aqueous.

As observed for the impedance spectrum in FIG. 27, only a slight variation is observed for both sensors on application of the deionised water. Unsurprisingly, a far greater variation is observed while the 23.3% NaCl droplet is applied. In this case, the unmodified sensor displays a sharp drop in impedance (almost three orders of magnitude) as the sensor is shorted by the highly conductive matrix; a large phase shift is also observed. In the case of the PTFE sensor, only a slight increase (~5%) is observed, less than that observed for deionised water. In addition, virtually no variation in phase shift is observed confirming that the solution is prevented from penetrating the PTFE film and shorting the sensor. Previously, we have employed commercial, free standing PTFE membranes as a means to allow dissolved ammonia partition from solution to a headspace and measure the response using an unmodified PANI sensor. To assess whether gaseous species are able to partition through the printed PTFE film from solution, a droplet of 50 ppm $NH_3$ was applied. In this case, the unmodified sensor displays a drop in impedance due to the ionic conductivity due to presence of ammonia in the form of dissociated ammonium and hydroxide ions within the droplet (the same principle as observed for the 23.3% NaCl solution). Despite the fact that the PANI is partially shifted from the ES form to the EB form, as evidenced by a colour change from green to blue, the resulting reduction in conductivity of the PANI is not picked up as the current flow is preferentially passed through the solution. For the modified sensor, the printed PTFE membrane again prevents the solution from interacting directly with the electrodes, resulting in a 50% increase in impedance due to the ES to EB conversion. This increase in impedance is due to the deprotonation of emeraldine salt to base and is observed for polyaniline on exposure to ammonia gas. This result demonstrates the possibility of using PTFE coated PANI as a means of detecting dissolved ammonia in solution, while minimising matrix effects and interfering species.

Impedance spectra were obtained after saline drops had been in contact with the film for 600 s. In contrast to the results obtained for deionised water, the unmodified PANI displays significant variation in both the magnitude and phase of impedance over the frequency range 0.01 Hz to 10 kHz. This is due to the capacitive (double-layer) effects that occur in the heavily ionic solution, as evidenced by the capacitive characteristics displayed for the PANI sensor on the Nyquist plot in the inset of FIG. 28. Similar results are obtained for the PANI sensors modified with 4 layers of PTFE, due to the failure of the membrane to prevent the solution from penetrating through to the PANI and electrodes. The sensors coated with 8 and 12 layers display comparatively little variation in impedance magnitude or phase shift, indeed both plots are near identical to that obtained for a sensor under dry conditions (Figure b).

A final test was performed to assess the effect of PTFE print thickness on the response to dissolved ammonia. In this case, 100 μL drops of 50 ppm ammonia in deionised water were applied to each sensor (FIG. 28). The unmodified sensor is included as comparison—again showing the drop in impedance due to ionic conductivity. Somewhat surprisingly, little variation is observed between the sensors modified with different print thicknesses of PTFE. The sensor modified with 4 layers has a slightly greater impedance response but those with 8 and 12 layers of PTFE display identical responses. Likewise, only a slight shift (~−0.5°) in phase angle is observed for each of the modified sensors. The response is relatively fast, approximately 120 s, after which a gradual drop in impedance is observed as the ammonia partitions out of the droplet and the concentration within steadily drops. In this instance, it appears that modification with relatively thin layers of PTFE is sufficient to protect the sensor from interference from water and allows for the dissolved ammonia to be detected.

The above results display the advantage of employing thin PTFE films over polyaniline sensors to discriminate against effects from moisture. This has many potential applications in aqueous-based sensing, however in this case the aim is to reduce effects from moisture in breath and allow for ammonia to be detected and quantified. To this end, the effect of PTFE on the detection of ammonia in the gas phase will be assessed in the following section.

Effect of PTFE Modification on Gaseous Ammonia Detection

In order to assess the effect of PTFE modification on the response of the PANI to gaseous ammonia, headspace analysis was performed. FIG. 29(a) shows the response of unmodified PANI and PANI sensors modified with different thicknesses of PTFE to increasing concentrations of ammonia in air while FIG. 29(b) shows the calibration plots obtained when the data is sampled 300 s after each injection. The results of linear regression are given in Table 1 below. The PTFE modification is seen to result in a major drop in sensitivity compared with the unmodified sensor. This indicates that the PTFE films may be impeding ammonia molecules from reaching the PANI layer. In addition, this could also be due to the partial deprotonation of PANI observed after printing. It was noted earlier that after printing PTFE, the measured resistance and impedance of the sensors was found to increase. Table 1 shows the measured resistance of each sensor and it can be seen that the resistance is approximately an order of magnitude higher for each of the PTFE modified sensors. This effect would also contribute to the reduction in sensitivity of the sensor as there would be fewer reaction sites within the partially deprotonated PANI film.

TABLE 1

Linear regression data for PANI-PTFE sensors. Experimental parameters as for FIG. 29.

| Composite | Initial R (kΩ) | Slope | Intercept | $R^2$ |
|---|---|---|---|---|
| PANI-PTFE 4 | 9.63 | 0.00732 | 0.997 | 0.9923 |
| PANI-PTFE 8 | 12.6 | 0.00714 | 0.996 | 0.9919 |
| PANI-PTFE 12 | 14.1 | 0.00649 | 0.997 | 0.9916 |
| PANI | 0.885 | 0.03130 | 0.892 | 0.9988 |

An initial test was performed using the artificial breath system to compare responses between the modified and unmodified sensors under ambient air conditions. FIG. 30 compares the response obtained when an unmodified PANI sensor and a PANI-PTFE sensor are exposed to gaseous ammonia under flowing conditions. Initially, ambient air was passed over the sensor at an approximate flow rate of 53.4 L min$^{-1}$. The ammonia cylinder was opened, exposing the sensors to a concentration of 280 ppb. This exposure continued for 600 s before the ammonia cylinder was closed for a further 600 s. This procedure was repeated four more times, yielding the response/recovery curves given in FIG. 30. In agreement with what was observed previously, it is clear that the modification of the sensor leads to a significant drop in the sensitivity of the device to ammonia. Without modification, the final three exposures display a normalised impedance of 1.25 while the PTFE modified sensor the corresponding result is 1.09.

Figure 31A:
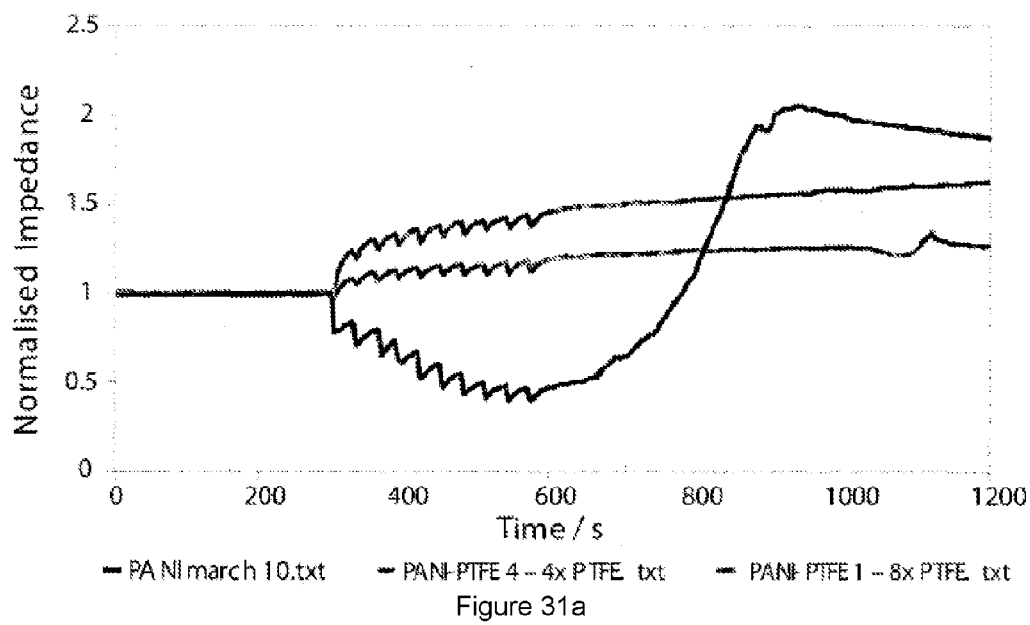
Figure 31B:
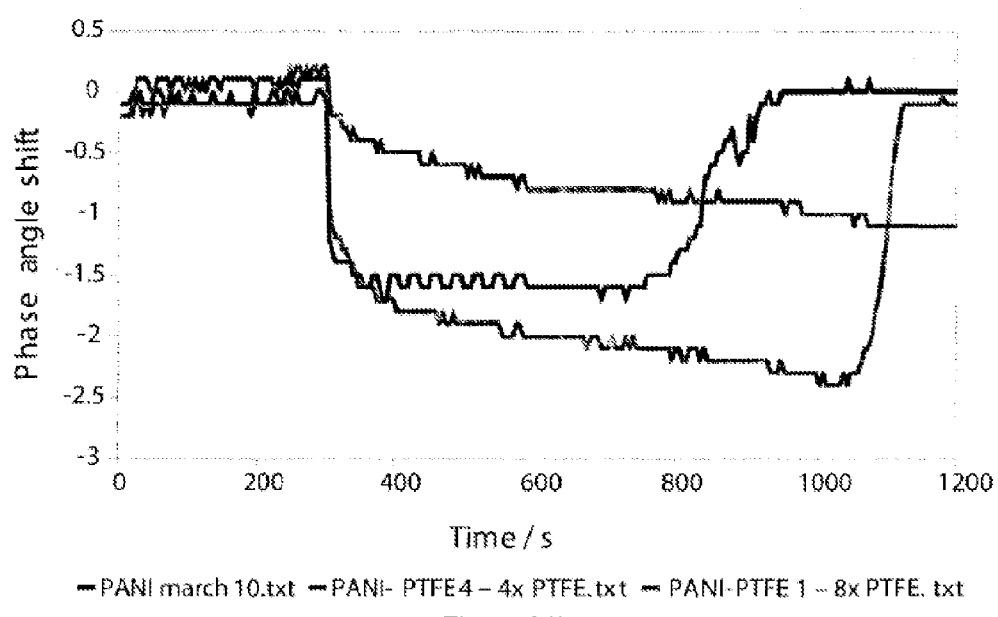

In FIG. 31, it is clear that both PTFE films prevent moisture from penetrating through to the PANI layer. The unmodified sensor displays very similar results to those observed previously when water drops containing 23.3% NaCl and 50 ppm ammonia were applied, with a noticeable drop in impedance and a negative shift in phase. This is unsurprising as the breath condensate would be expected to contain dissolved ionic species that would result in some conduction through solution and a capacitive characteristic. The sensor modified with four layers of PTFE also correlates with the early behaviour in that an increase in impedance is observed, implying the presence of ammonia, coupled with a negative shift in phase angle, implying a capacitive effect due to some of the condensate penetrating the PTFE layer. The eight layer PTFE film displays the best effect under these conditions with the greatest impedance increase coupled with the smallest phase shift.

In conclusion, inkjet printable formulations of PTFE microparticles or nanoparticles have been used in a variety of versatile analytical applications: from patterning channels for fluid flow to gas permeable, hydrophobic layers on sensors. When used on sensors, they allowed for short term analyses to be performed on liquid samples e.g. dissolved ammonia in aqueous drops. In terms of reducing condensing effects during gas phase ammonia analysis of humid systems, these printed layers significantly reduced moisture effects. However, sensitivity to ammonia was also significantly reduced. This was possibly due to a combination of effects including the PTFE film impeding ammonia molecules from reaching the PANI layer and a partial deprotonation of the PANI during the printing of the PTFE layer. This latter effect could be reduced or eliminated by introducing a reprotonation step after synthesis—possibly involving exposure to gaseous acidic species.

At a fundamental level, the problem with all clinical interventions is the need to perform some form of 'test' on a patient to diagnose or monitor diseases and treatments. These tests come in many forms, but typically involve measuring some physiological marker inside the patient. The vast majority of physiological markers are present in either blood or tissue, which require blood sampling or biopsy. Both of these procedures are invasive, painful, relatively costly and not always available at the point of care. This has consequences for both the patient and the clinician and tends to result in the avoidance of, or reduced frequency of testing, even if such would bring about improved patient outcomes. For patients, fear, pain and discomfort are all brought about by invasive procedures. Clinicians tend to adjust their testing regimes in relation to their cost, convenience and the level of diagnostic and prognostic information they obtain. It also makes invasive testing difficult in many patient types such as neonates, young children, the mentally ill and the elderly. Consequently, diagnosis is slower and treatment procedures may be overly long (e.g., continuing haemodialysis even after blood urea has reached baseline levels). Invasive procedures also require expensive laboratory testing and so are performed sparingly and infrequently. The overall effect is to reduce the overall frequency of testing. Other sources of test material for patients include urine, faeces, sweat and breath. Clearly, breath offers many advantages as a test material, being gaseous, and essentially free from pathogenic risks such as HIV, Hepatitis and other infectious agents carried in blood, urine and faeces. It is 'clean' and does not require any disposal. Many conditions are also amenable to diagnosis or therapeutic monitoring using breath analysis as species present in exhaled breath correlate with, or correspond to physiological markers in the blood and tissue. With regards to ammonia, it has been shown that breath ammonia levels correlate with blood urea nitrogen (BUN) and creatinine levels in patients with end-stage renal (kidney) failure and can be used to monitor haemodialysis. Ammonia has also been identified as a marker of liver dysfunction in hepatic encephalopathy. It can be used to diagnose *H. pylori* infection and halitosis and in sports physiology.

The system 100 (or 200) of the present specification provides means for monitoring ammonia in breath in real time with convenience using a relatively low cost, compact sized, portable breath monitoring device. The arrangement is advantageous over prior approaches for measuring ammonia which are often bulky, complex and expensive and cannot be readily miniaturised, or are not analytically capable of the physiological measurement of ammonia and further which cannot operate in real time. For example, often breath must be collected, concentrated and sampled 'off-line' due to issues of system sensitivity and complexity. This means that few systems can collect real-time data for continuous patient monitoring and those that can, cannot do it at point-of-care.

The system of the present specification provides a real time point-of-care system for monitoring breath ammonia. However, there are several techniques available for measuring breath ammonia, some of which have been used clinically and others which have not been applied to this area. The most successful technologies thus far to measure physiological ammonia in breath have been the instrumental methods such as spectroscopies including laser, diode laser, optoacoustic and cavity ring down traditional gas chromatography-mass spectrometry and other forms of mass spectrometry including selected ion flow tube, and atmospheric pressure ionization (API-MS) have also been used. Such systems have clear and obvious limitations. For example, many optical spectroscopic technologies are also only qualitative or semi-quantitative techniques, requiring comparisons with libraries of spectra to define a condition, rather than a quantitative measurement of the analytes.

The system of the invention comprises a sensing electrode fabricated from polyaniline nanoparticles. The polyaniline nanoparticles may as described be deposited by inkjet printing. The arrangement has several advantageous results. It improves the manufacturing reproducibility of the devices, making them simple and straightforward to calibrate, as well as making them low cost and easily producible and further amenable to single test/disposability. In addition, the quality of the printed nanoparticulate films has improved the limit of detection achievable with these sensors to levels which are suitable for diagnostic monitoring applications. These sensor electrodes are capable of quantitative analysis at just 12 ppb, which is below the requirements for diagnostic breath monitoring, where 50 ppb is the desired target. The arrangement of the present specification accordingly provides a combination of performance and device cost which makes this suitable for point of care applications.

Advantageously, the method, device and system provided by the present specification relates specifically to the removal of any effects of humidity, temperature and condensation to allow for the measurement of ammonia. The key issues that need to be overcome in order to measure ammonia in the breath are the temperature and humidity of the breath and also controlling the volume and flow rate of the breath sample. The device, system and method as described herein removes temperature and humidity signals so in effect and all that is left is the ammonia signal. The ammonia signal is the focus. The method of removing humidity and temperature sensitivity of the polyanaline sensor involves alternating between ambient air and breath. The method then further provides for exploiting the slow dissociation rate of ammonia from the PANI-sensor (presumably versus a faster dissociation rate of water molecules). The device of the present application then provides a synergistic combination of features which support the above described method. In effect the effects of temperature and water vapour can be differentiated from the measurement of ammonia. Advantageously there is provided a system and method which allows the quantitative measurement of ammonia in breath samples across the diagnostically relevant ranges.

The arrangement described advantageously provides a sensor which required minimal calibration and which show excellent intra-electrode baseline drift. The arrangement provides that gases typically present in breath do not interfere with the sensor. Temperature and humidity effects are distinguishable from the response of the sensor to ammonia. The arrangement provides a response with a single simulated breath. Quantification was improved after a number of breaths.

The breath ammonia monitoring system of the prior art have been found unsuitable as a point of care device for monitoring ammonia in breath. To achieve measurement of ammonia, the gas must be sequentially dissolved in acidic and basic solutions before being measured using a simple conductivity probe. The need to supply multiple liquids requires reservoirs, pumps and waste chambers, which makes this system cumbersome. In addition, the measurement is highly non-specific and lacking in sensitivity below 1 ppm, which is well above the range required for biomedical applications where 50 ppb is required.

The other key aspects of this invention are its ability to perform measurements of ammonia at physiologically relevant levels in real time and in a real breath sample matrix. The system of the invention advantageously compensates for breathing rates and volumes, interferences from humidity, temperature and other potentially interfering gasses and volatile species present in the breath. The system of the present specification offers a range of device design solutions which relate to additional sensor modifications, the breath sampling interface and the signal processing methodology which results in the extraction and isolation of responses in real breath samples that relate only to the ammonia content. No other non-instrumental, sensor-based system has achieved this. Bulky and expensive instrumental systems can achieve such outcomes but are not amenable to point of care testing in the manner of the present device.

The sensor arrangement, sampling methods and signal processing techniques are new and advantageous. The arrangement provides unexpected results and as no one else has yet achieved the ability to use materials of the type used in the system of the present specification for real diagnostic breath measurement applications.

Detection of ammonia as the basis of clinical testing has applications in measurement of kidney and liver (dys) function (screening, monitoring and treatment support), the diagnosis of hepatic encephalopathy, for monitoring the effects of haemodialysis in patients with end-stage renal disease, in both the hospital and emerging home dialysis (intra-peritoneal) market, diagnosing *Helicobacter pylori* gastric infections (ulcers), diagnosis of halitosis and in exercise physiology.

The system of the present specification provides for a portable testing device for breath ammonia. The system advantageously provides an early warning type system as it may be used by patients directly (e.g. home testing) and at GP clinics obviating the need for a patient to attend at hospital or clinic which may involve a waiting period. As a portable testing device for breath ammonia, the system may also be advantageously used for ongoing monitoring, supplementing the suite of tests performed at the clinic, and allowing the patient more freedom. Further advantageously in comparison with previously available approaches, the system of the invention provides a relatively a low-cost and point-of-care/home testing solution.

The words comprises/comprising when used in this specification are to specify the presence of stated features, integers, steps or components but does not preclude the presence or addition of one or more other features, integers, steps, components or groups thereof.

The invention claimed is:

1. A system for sensing and measuring ammonia in a breath sample, comprising:
   an ammonia sensor, and
   a sampling means for capturing and directing a breath sample from a subject to the ammonia sensor,
   wherein:
   the ammonia sensor comprises a conducting polymer polyaniline sensor, and
   the sampling means comprises a capture chamber, the capture chamber having an inlet and outlet and a capture chamber volume defined by the dimensions of the capture chamber, wherein the capture chamber provides a breath sample of predefined volume from the capture chamber across the ammonia sensor,
   the inlet having a first valve through which a breath is exhaled into the capture chamber, and
   the outlet having a second valve through which breath surplus to the volume of the capture chamber is expelled.

2. The system of claim 1, wherein the sampling means comprises directing means for directing the breath sample of predefined volume from the capture chamber across the ammonia sensor.

3. The system of claim 2, wherein the directing means is operable to direct the breath sample of predefined volume across the sensor at a predefined volume flow rate.

4. The system of claim 1, wherein the sensor has a response to the breath sample, and wherein the response from the sensor is proportional to a concentration of ammonia in the breath sample.

5. The system of claim 1, comprising measuring means for measuring change in conductivity or impedance of the sensor on exposure to ammonia in the breath sample, the change in conductivity or impedance being indicative of ammonia concentration in the breath sample.

6. The system of claim 1, the sensor comprising one of:
   a polyaniline nanoparticle based material;
   a polyaniline composite;
   a PANI-silver composite; or
   a PANI-carbon nanotube composite.

7. The system of claim 1, wherein the sensor is integrated with a heater configured in operation to control response of the sensor to ammonia.

8. The system of claim 1, the sensor comprising a membrane layer applied to the sensor for protecting the sensor from humidity in the breath sample while allowing detection of ammonia.

9. The system of claim 8, wherein the membrane layer is in the form of a pre-fabricated membrane.

10. The system of claim 8, wherein the membrane layer is a printable membrane layer.

11. The system of claim 8, wherein the membrane layer is of a membrane material impermeable to water molecules.

12. The system of claim 8, wherein the membrane layer is of polytetrafluoroethene, or other polymer material permeable to ammonia gas and having water repellent properties.

13. The system of claim 8, wherein the membrane layer comprises a solubilised polymer or a suspension of micro- or nanoparticles.

14. The system of claim 13, wherein the particles are dispersible in aqueous solvents and annealeable to form a continuous film upon application of heat, and/or light energy and/or chemical treatment.

15. The system of claim 1, the sensor comprising a membrane layer applied to the sensor for controlling a response of the sensor to humidity in the breath sample.

16. The system of claim 1, wherein the volume of the capture chamber is of the order 0.25 to 0.5 of an average human non-forced exhalation of breath.

17. The system of claim 1, the sampling means comprising displacement means configured to provide displacement of any air or other sample present in the capture chamber prior to capture of a breath sample.

18. The system of claim 1, the sampling means including a sampling interface for interfacing with the subject whose breath is to be sampled, the sampling interface comprising a mask or spirette.

19. The system of claim 18, wherein a bacterial or viral filter is provided located between the interface and sample capture chamber.

20. A point of care testing device comprising a system for sensing and measuring ammonia in a breath sample as claimed in claim 1, wherein the device is configured to provide a real time measurement of the concentration of ammonia in a breath sample.

21. A point of care testing device comprising a system for sensing and measuring ammonia in a breath sample as claimed in claim 1, wherein the device is configured to provide a continuous monitoring of ammonia in a breath sample over a period of time.

22. A method of sensing ammonia in a breath sample comprising:
  capturing a breath sample of predefined volume in a capture chamber having an inlet and an outlet, wherein dimensions of the capture chamber define the predefined volume, the inlet includes a first valve through which a breath is exhaled into the capture chamber, and the outlet includes a second valve through which breath surplus to the volume of the capture chamber is expelled;
  directing the breath sample of predefined volume across an ammonia sensor comprising a conducting polymer polyaniline sensor; and
  measuring a response of the sensor to ammonia in the breath sample.

23. A method as claimed in claim 22 wherein measuring the response of the sensor comprises measuring a change in conductivity or impedance of the sensor on exposure to ammonia in the breath sample, the change in conductivity or impedance being proportional to an ammonia concentration in the breath sample.

24. A method as claimed in claim 22 wherein the directing the breath sample across the sensor comprises: directing the breath sample across the sensor at a defined and/or at a measurable volume flow rate.

25. A system for sensing and measuring ammonia in a breath sample, the system comprising:
  an ammonia sensor comprising a conducting polymer polyaniline sensor and a membrane layer applied to the sensor and configured to protect the sensor from humidity in breath sample while allowing detection of ammonia; and
  a sampling means for capturing and directing a breath sample from a subject to the ammonia sensor, the sampling means comprising a capture chamber having an inlet and an outlet, wherein dimensions of the capture chamber define a predefined volume, the inlet includes a first valve through which a breath is exhaled into the capture chamber, and the outlet includes a second valve through which breath surplus to the volume of the capture chamber is expelled.

* * * * *